(12) United States Patent  (10) Patent No.: US 7,905,892 B2
Nobles et al.  (45) Date of Patent: Mar. 15, 2011

(54) SUTURE CUTTER

(75) Inventors: Anthony A. Nobles, Fountain Valley, CA (US); Steven E. Decker, Anaheim, CA (US); Rod T. Peterson, Santa Ana, CA (US)

(73) Assignee: Nobles Medical Technologies, Inc., Fountain Valley, CA (US)

( * ) Notice: Subject to any disclaimer, the term of this patent is extended or adjusted under 35 U.S.C. 154(b) by 1214 days.

(21) Appl. No.: 10/842,031

(22) Filed: May 7, 2004

(65) Prior Publication Data

US 2004/0210238 A1  Oct. 21, 2004

Related U.S. Application Data

(63) Continuation of application No. 09/940,384, filed on Aug. 27, 2001, now Pat. No. 6,733,509.

(60) Provisional application No. 60/228,267, filed on Aug. 25, 2000.

(51) Int. Cl.
    A61B 17/04  (2006.01)
(52) U.S. Cl. ....................................................... 606/144
(58) Field of Classification Search .................. 606/138, 606/232, 139, 144, 148
    See application file for complete search history.

(56) References Cited

U.S. PATENT DOCUMENTS

| | | | |
|---|---|---|---|
| 3,665,926 A | 5/1972 | Flores | |
| 4,662,068 A | 5/1987 | Polonsky | |
| 5,021,059 A | 6/1991 | Kensey et al. | |
| 5,160,339 A | 11/1992 | Chen et al. | |
| 5,171,251 A | 12/1992 | Bregen et al. | |
| 5,222,974 A | 6/1993 | Kensey et al. | |
| 5,242,459 A | 9/1993 | Buelna | |
| 5,282,827 A | 2/1994 | Kensey et al. | |
| 5,336,231 A | 8/1994 | Adair | |
| 5,403,331 A * | 4/1995 | Chesterfield et al. | 606/148 |
| 5,423,837 A | 6/1995 | Mericle et al. | |
| 5,439,470 A | 8/1995 | Li | |
| 5,452,513 A * | 9/1995 | Zinnbauer et al. | 30/140 |
| 5,520,702 A | 5/1996 | Sauer et al. | |
| 5,545,170 A | 8/1996 | Hart | |
| 5,565,122 A * | 10/1996 | Zinnbauer et al. | 219/227 |
| 5,593,422 A | 1/1997 | Muijs Van de | |
| 5,669,917 A | 9/1997 | Sauer et al. | |
| 5,700,277 A | 12/1997 | Nash et al. | |
| 5,766,183 A * | 6/1998 | Sauer | 606/139 |
| 5,860,990 A | 1/1999 | Nobles et al. | |
| 6,068,648 A * | 5/2000 | Cole et al. | 606/232 |
| 6,077,277 A | 6/2000 | Mollenauer et al. | |
| 6,099,553 A | 8/2000 | Hart et al. | |
| 6,117,144 A | 9/2000 | Nobles et al. | |
| 6,159,234 A | 12/2000 | Bonutti et al. | |
| 6,174,324 B1 * | 1/2001 | Egan et al. | 606/232 |
| 6,187,026 B1 | 2/2001 | Devlin et al. | |
| 6,217,591 B1 * | 4/2001 | Egan et al. | 606/144 |
| 6,432,115 B1 * | 8/2002 | Mollenauer et al. | 606/148 |
| 6,562,052 B2 | 5/2003 | Nobles et al. | |
| 6,733,509 B2 | 5/2004 | Nobles et al. | |

FOREIGN PATENT DOCUMENTS

| | | |
|---|---|---|
| WO | WO 98/12970 | 4/1998 |
| WO | WO 00/02489 | 1/2000 |
| WO | WO 95/25470 | 9/2009 |

* cited by examiner

*Primary Examiner* — (Jackie) Tan-Uyen T Ho
*Assistant Examiner* — Gregory Anderson

(57) ABSTRACT

Suture cutter embodiments include elements for cutting back the leads of a suture after the suture has been tied into a knot, e.g., as a result of drawing tissue portions together. The suture cutter may include mechanisms which can be used to push and position a knot, so that a single device may be used to both push a knot and trim the excess material therefrom.

1 Claim, 35 Drawing Sheets

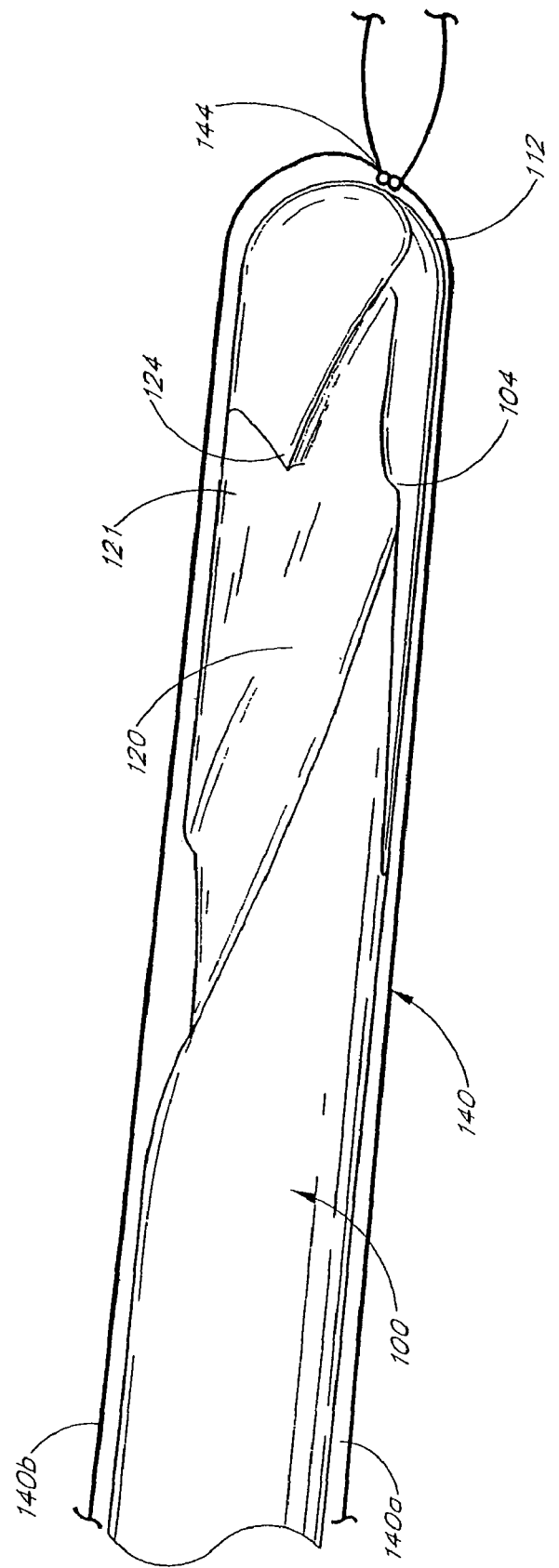

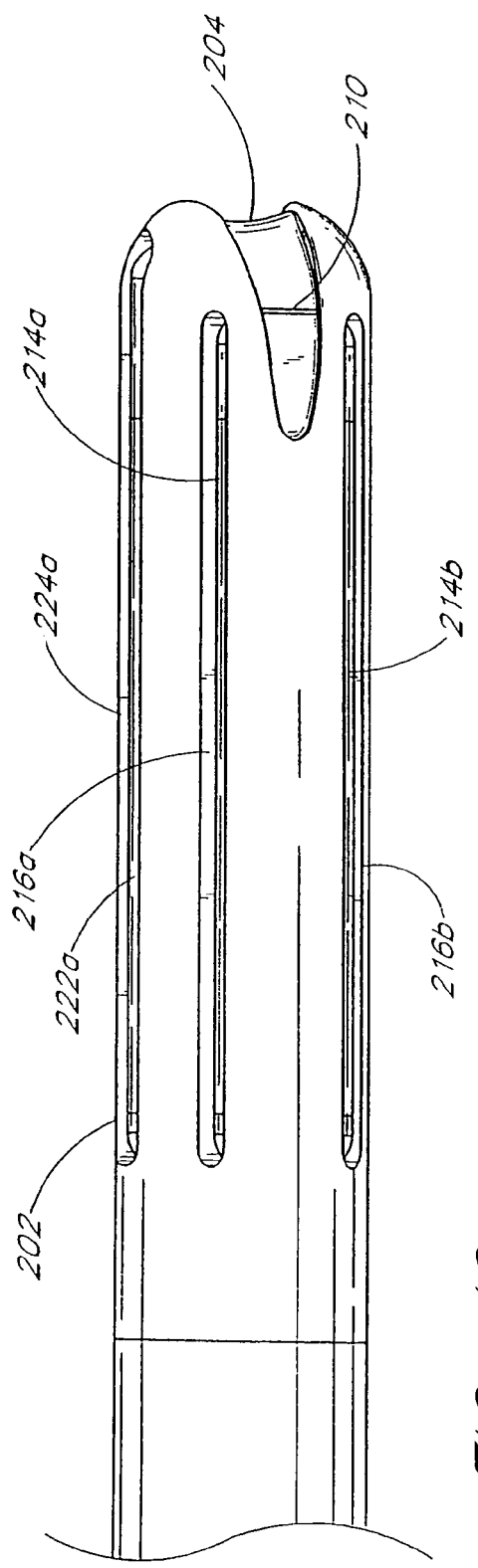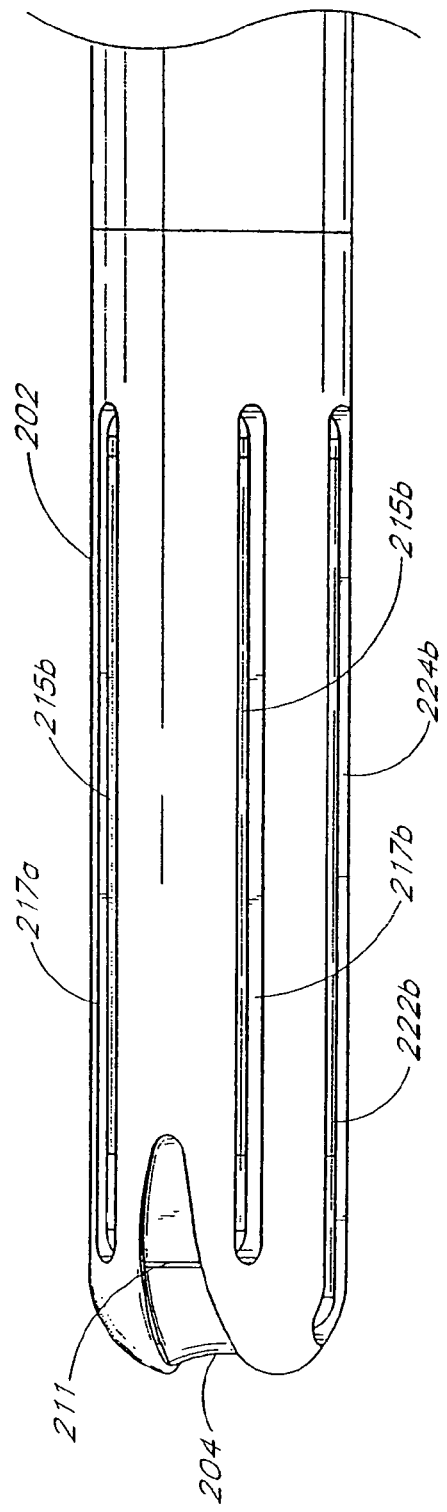
FIG. 10
FIG. 11

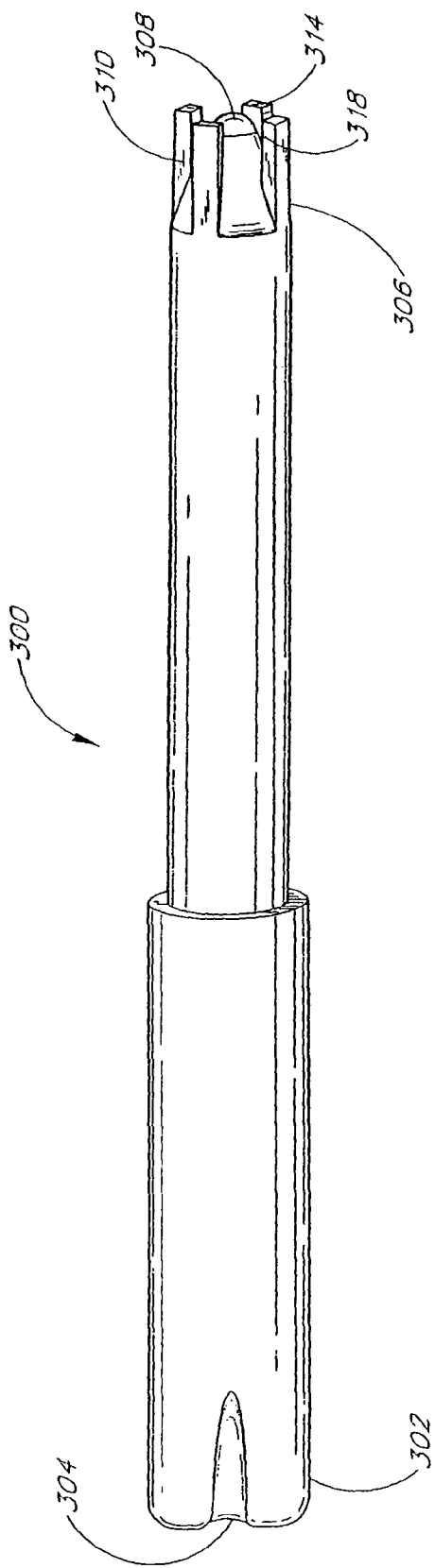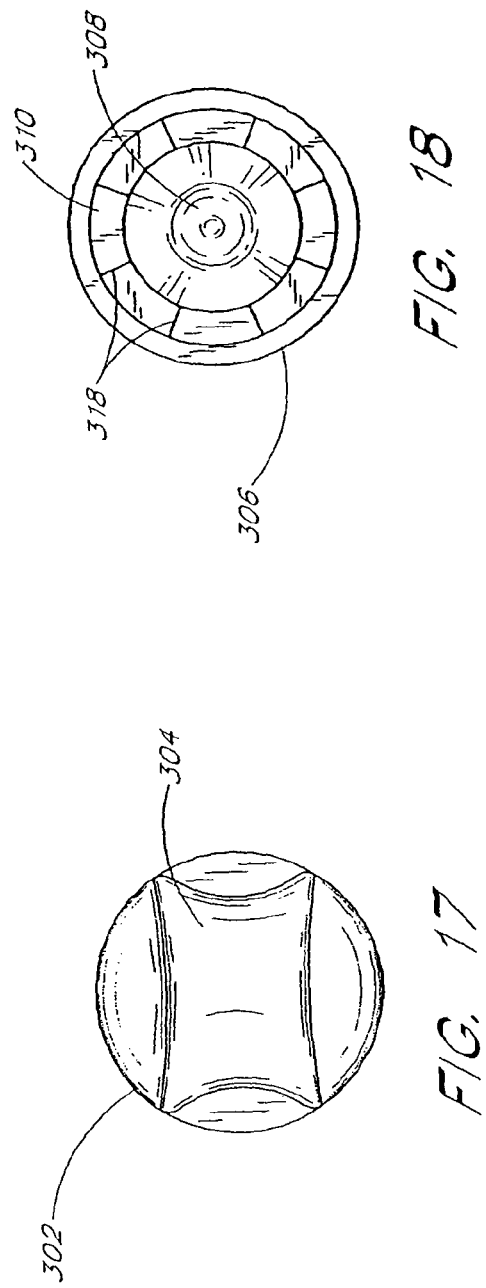
FIG. 16
FIG. 18
FIG. 17

SUTURE CUTTER

CROSS-REFERENCE TO RELATED APPLICATION

This application is a continuation of U.S. application Ser. No. 09/940,384, filed Aug. 27, 2001, now U.S. Pat. No. 6,733,509, which also claims the benefit of U.S. Provisional Application Serial No. 60/228,267, filed Aug. 25, 2000, now abandoned, the entirety of which is hereby incorporated by reference.

BACKGROUND OF THE INVENTION

1. Field of the Invention

The invention relates to suturing incisions, and more specifically, to the use of sutures for closing incisions in vessels and organs within a body, and cutting the ends of a suture once it has drawn together tissue portions.

2. Description of the Related Art

Surgeons frequently encounter the need to close incisions, wounds, or otherwise join tissue portions with a suture. After passing the suture through the tissue portions, the surgeon must tie the suture to draw the tissue portions together and prevent them from separating. When sutures are tied in a region having restricted access, such as the end of a tissue tract leading to an artery, the surgeon is presented with special challenges. Typically, the knot is formed outside the patient and then is pushed towards those tissue portions to be joined together.

Once a knot has been positioned against tissue portions such that they are securely fastened together, however, the surgeon must cut back the ends of the suture. This procedure can be difficult when using conventional instruments, particularly where access is limited. A reliable suture cutting procedure is needed whereby a surgeon can rapidly and accurately trim back the strands from a knot.

SUMMARY OF THE INVENTION

According to one aspect of the invention, there is provided a method of severing end portions of a suture which extend from a sutured tissue portion. The method includes holding the suture end portions, and positioning an elongate member such that a distal portion of the elongate member is adjacent the sutured tissue portion. The method further includes positioning the suture end portions within at least one receptacle disposed at the distal portion of the elongate member, and severing the suture while the suture end portions are within said at least one receptacle by activating a severing element disposed adjacent the receptacle.

According to another aspect of the invention, there is provided an apparatus which includes a receptacle for juxtaposing portions of a suture to be connected to each other. The apparatus further includes a collar configured to surround the juxtaposed portions and a compression element positioned to compress the collar against the suture portions.

BRIEF DESCRIPTION OF THE DRAWINGS

FIGS. 1-7 illustrate a first suture cutter embodiment, in which:

FIGS. 1 and 2 are end views of the suture cutter.

FIGS. 3B, 4B, and 5B correspond to the side elevation views of FIGS. 3A, 4A, and 5A, and show the suture cutter being used with a suture;

FIG. 6 illustrates the suture cutter pushing a knot into a patient through a catheter sheath introducer (CSI);

FIGS. 8-15 illustrate a second suture cutter embodiment, in which:

FIGS. 8 and 9 show perspective views of the distal end of the suture cutter;

FIGS. 10 and 11 show side views of the distal end of the suture cutter;

FIG. 12 shows the full length of the suture cutter including the handle;

FIGS. 13 and 14 show the suture cutter with a suture, before and after the suture is thermally cut, respectively; and FIG. 15 shows the suture cutter being used to twist the suture ends.

FIGS. 16-24 illustrate a third suture cutter embodiment, in which:

FIG. 16 shows a first cylindrical member, which has one end that acts like a knot pusher and another end that includes blade members for cutting suture material;

FIG. 17 is a view of the knot pusher end of the first cylindrical member;

FIG. 18 is a view of the blade member end of the first cylindrical member;

FIG. 19 shows a second cylindrical member, which at one end has an extension member for rotating the second member, and at the other end has blade members for cutting suture material;

FIG. 20 is a view of the blade member end of the second cylindrical member;

FIG. 21 shows the assembled suture cutter, in which the second cylindrical member has been slid over the first cylindrical member;

FIG. 22 shows the blade member end of the assembled suture cutter; and

FIGS. 23 and 24 show the suture cutter with a suture, before and after the suture is cut, respectively, in which the suture is cut by rotating the second cylindrical element with respect to the first cylindrical element.

FIGS. 25-28 illustrate a fourth suture cutter embodiment, in which:

FIG. 25 shows an expanded, isometric view of the distal end of the suture cutter;

FIG. 26 is a cutaway which shows a welding element and a cutting element housed inside a compression tip for pressing a suture cylinder against ends of a suture;

FIG. 27 shows a lump of suture material (which functions as a knot) which is formed when the suture and the suture cylinder are acted upon by the suture cutter;

FIG. 28 shows another expanded, isometric view of the distal end of the knot pusher;

FIGS. 29-33D illustrate a fifth suture cutter embodiment, in which:

FIG. 29 is a perspective view showing how the suture cutter captures ends of a suture with a lasso;

FIG. 30 is a cross sectional view of the cutter as it is configured in FIG. 29;

FIG. 31 shows the lasso having drawn the suture ends though and out of a hypotube;

FIG. 32 is a cross sectional view of the cutter as it is configured in FIG. 31;

FIGS. 33A-D illustrate sequentially how a suture collar positioned in the cutter is used to form a fused portion in the suture which then acts like a knot.

DETAILED DESCRIPTION OF THE PREFERRED EMBODIMENT

Preferred embodiments of the invention are shown and described with respect to the accompanying figures. The suture cutters herein may be used to cut the free ends of a suture extending from a knot that has closed up an incision within a patient (e.g., an incision in an organ or a vessel), or more generally, two tissue portions that have been drawn together.

Figure 1:
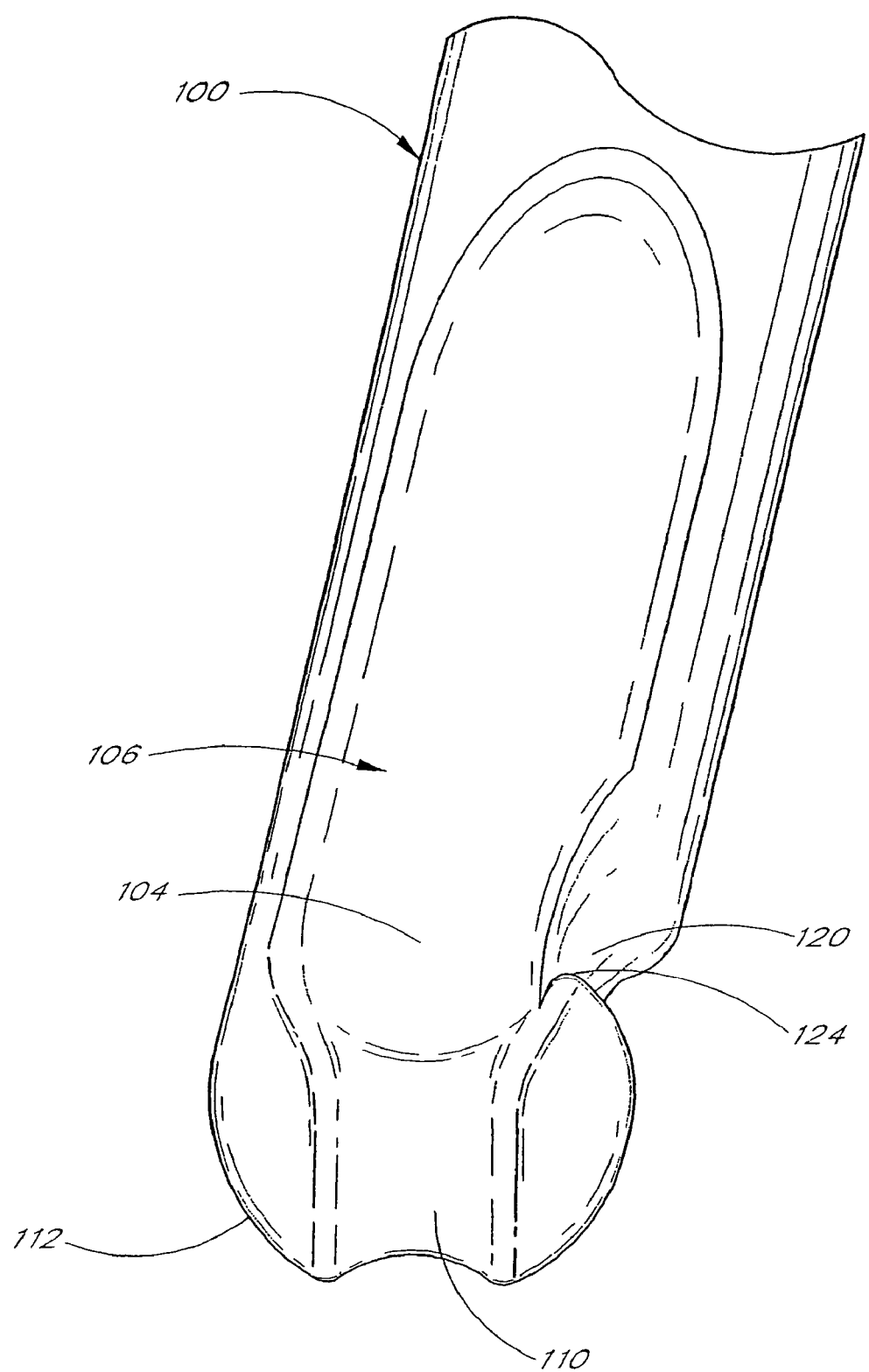

An end view of a first suture cutter embodiment is shown in FIG. 1. The suture cutter comprises an elongated, rod-shaped member 100 which includes an elongate recess 106 that extends longitudinally along opposed sides of the member 100 and transversely across the distal end 112 of the member 100. The recess 106 thus includes a first longitudinal recessed portion 104, a transverse recessed portion 110 at the distal end 112 of the elongate member 100, and a second longitudinal recessed portion 116 shown in FIG. 2, in which the member 100 has been rotated 180 degrees about its longitudinal axis with respect to its orientation in FIG. 1. The second recessed portion 116 is somewhat shallower and narrower than the recessed portions 104, 110. The longitudinal portions 104, 116 gradually taper from the distal end 112 of the elongate member 100 into the exterior surface of the member 100. The recessed portions 104, 110 and 116 are shaped as channels having semi-circular or semi-elliptical cross sections, such that ends extending from a surgical knot can be effectively guided within the recessed portions 104, 116 and the knot can be pushed by the recessed portion 110 of the member 100.

Figure 2:
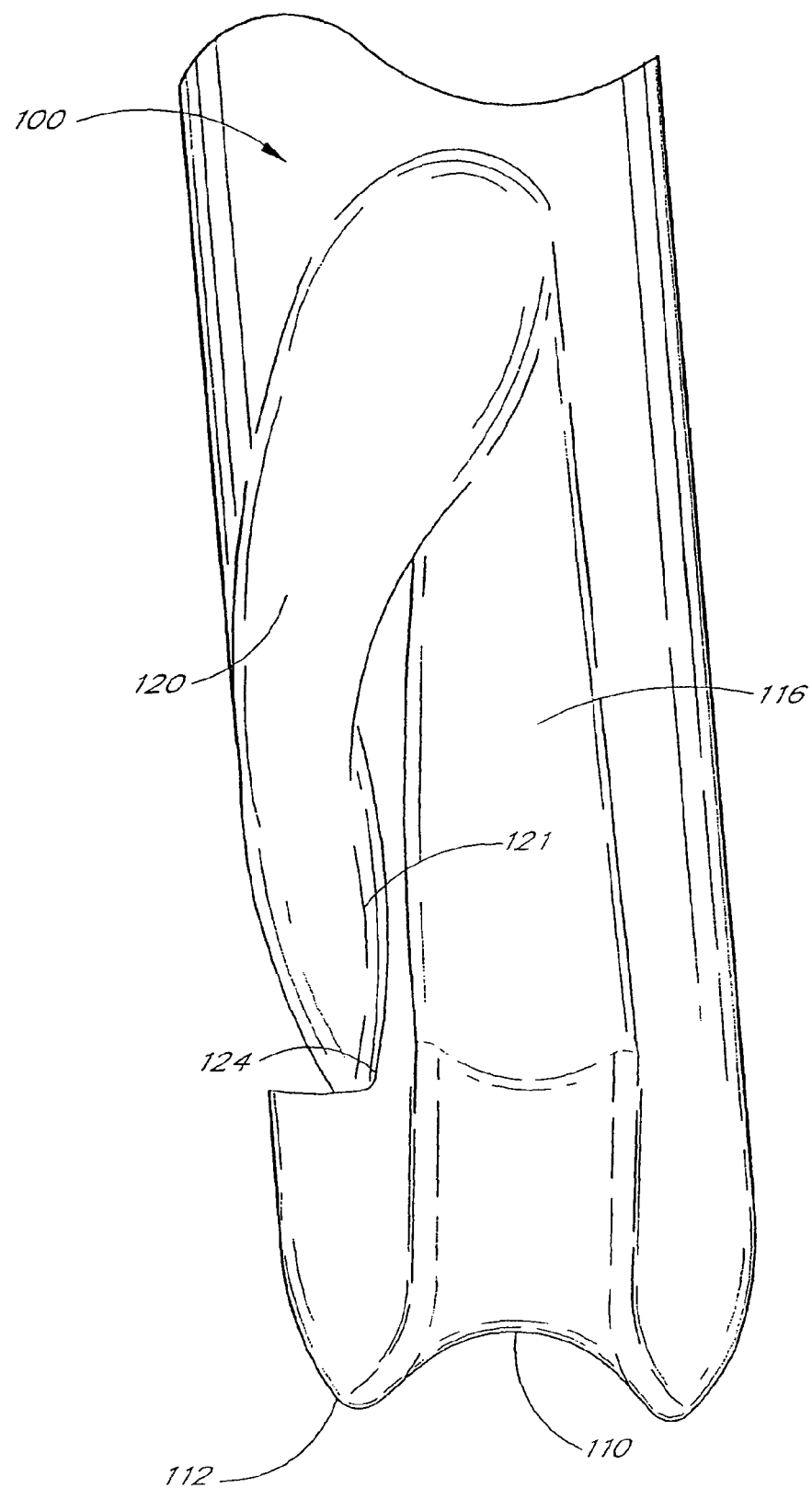
Figure 3A:
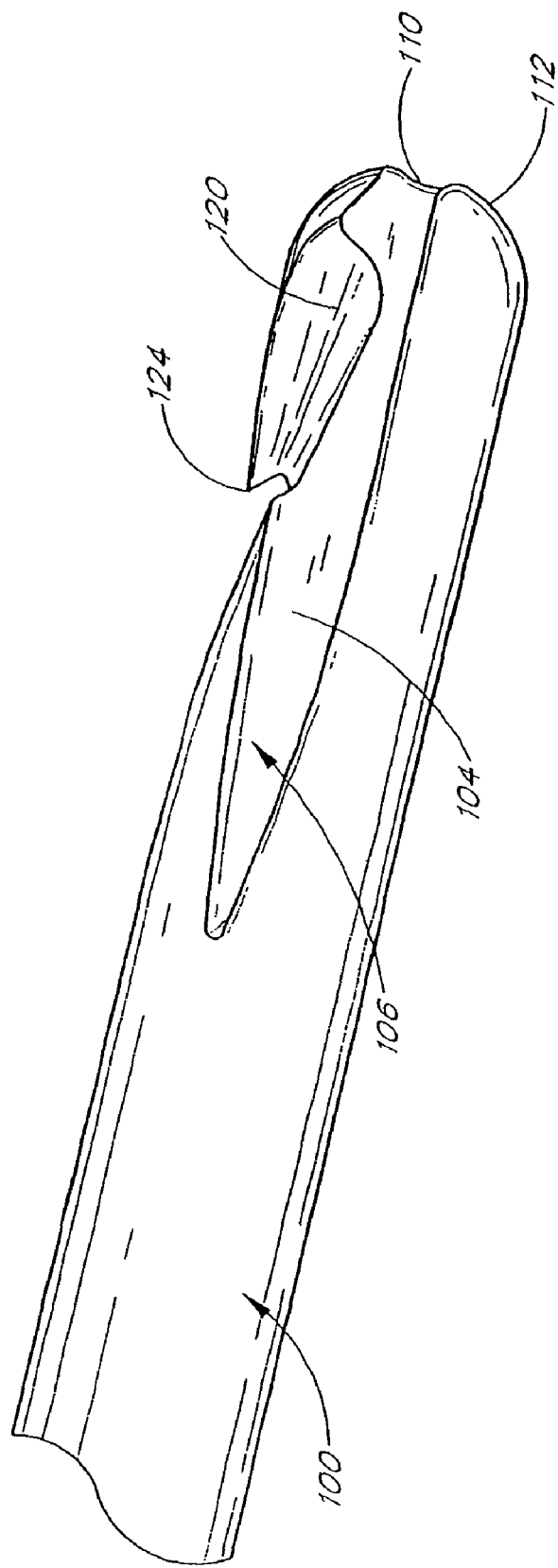
FIGS. 3A, 4A, and 5A are side elevation views of the suture cutter.
Figure 4A:
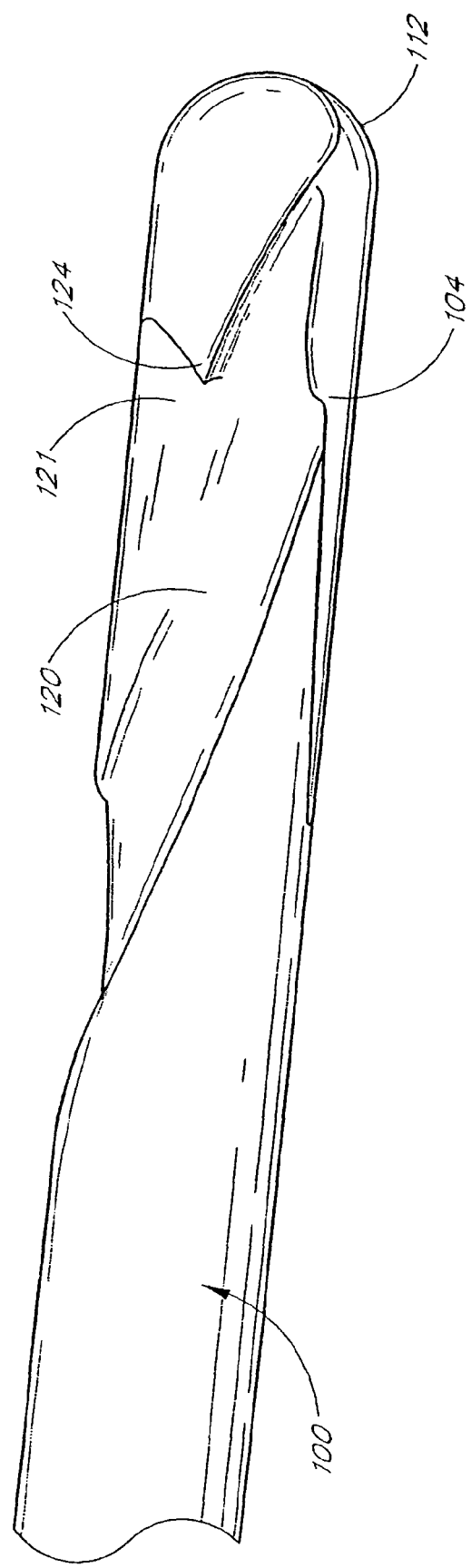
Figure 5A:
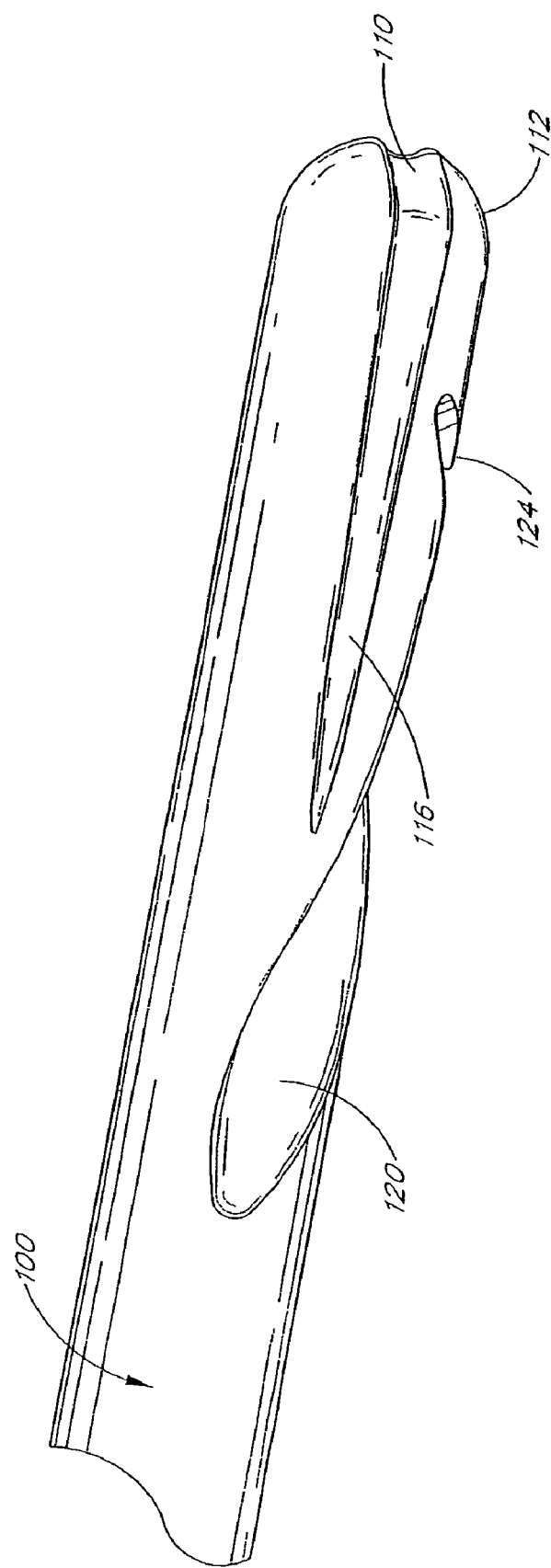

An angled recess 120 extends between the first and second recessed portions 104, 116 along a side of the elongate member 100 at an angle relative to the longitudinal axis of the member 100. The recess 120 intersects the recessed portion 104 near the juncture of the portion 104 with the transverse portion 110. The recess 120 intersects the portion 116 at a location which is a significant distance proximal of the distal end 112. As indicated in FIGS. 1 and 2, a cutting element 124 is provided at the end of the recess 120 that is next to the transverse portion 110. The cutting element 124 comprises a cutting edge that is directed proximally and is formed by a recess 121 that extends generally orthogonal to the recess 120 and between the recess 120 and the recessed portion 116. The recesses 120 and 121, as well as the cutting element 124 are more clearly shown in FIGS. 3A, 4A, and 5A, which are oriented at 120 degrees (about the longitudinal axis) with respect to each other.

Figure 3B:
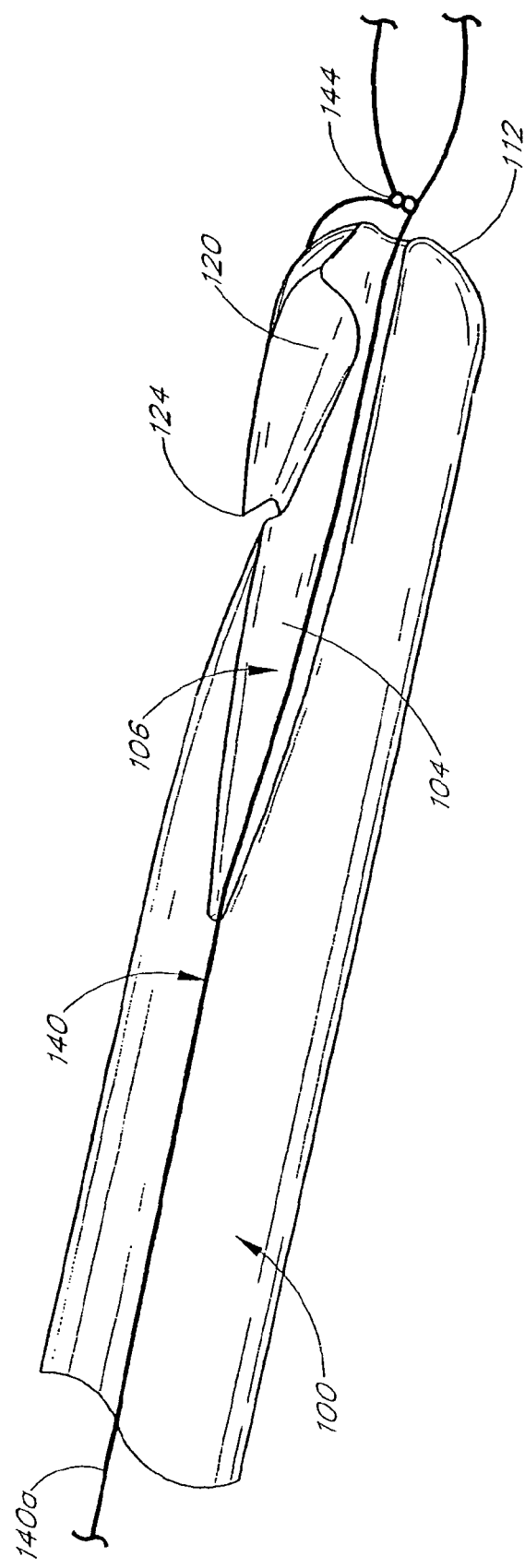
Figure 5B:
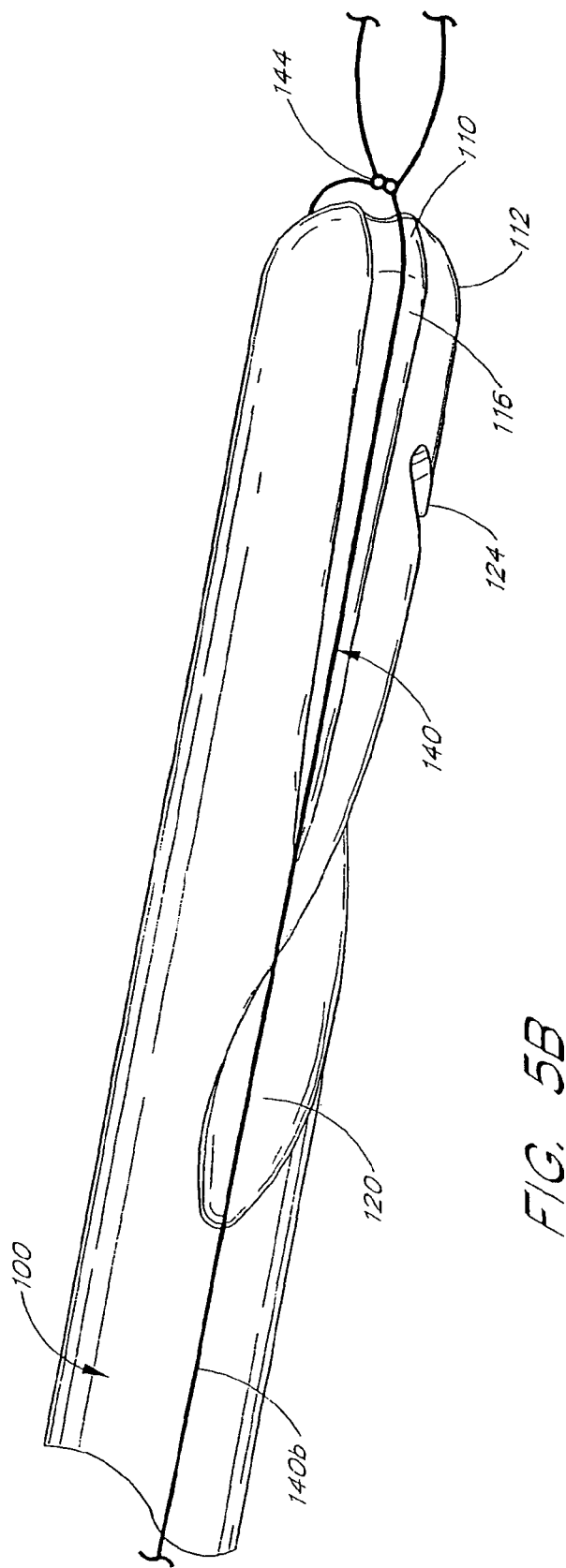

FIGS. 3B, 4B, and 5B show the member 100 used with a suture 140 which has been tied into a self cinching knot 144. The member 100 is oriented so that respective end segment portions 140a, 140b of the suture are disposed resting along and within the longitudinal recessed portions 104, 116, respectively, with the transverse portion against the knot 144. The knot 144 may be formed as described in Applicant's copending application entitled "Knot Pusher", Ser. No. 09/571,759 filed on May 15, 2000 which is hereby incorporated by reference herein. In one embodiment, the suture 140 is a monofiliment suture having a diameter of about 0.010". It may be introduced into the patient as described in U.S. Pat.

Figure 6:
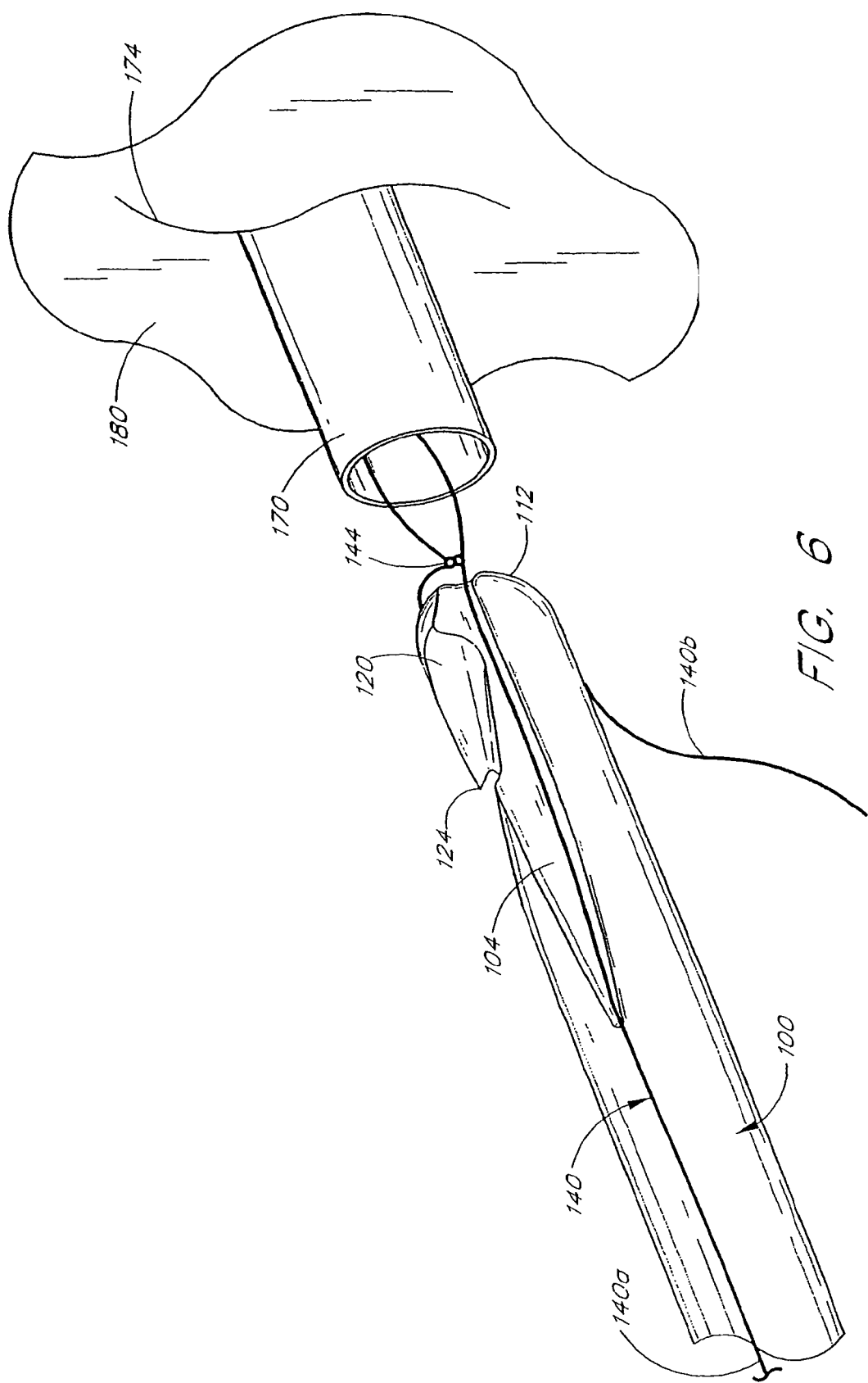

No. 5,860,990 entitled "Method and apparatus for suturing" and Applicant's copending application Ser. No. 09/524,211 filed Mar. 13, 2000 entitled "Suturing device and method", both of which are hereby incorporated by reference herein. As described in more detail in the aforementioned copending application entitled "Knot Pusher", the practitioner may form a knot 144 utilizing a variety of knot tying techniques. One example is to tie two consecutive half hitches of the same orientation (e.g., two right hitches or two left hitches). One end segment of the suture 140 (e.g., the end segment 140b) remains loosely hanging off to the side while the practitioner pushes the distal end 112 of the elongate member 100 against the knot 144, with the knot 144 in the recessed portion 110. The member 100 fits snugly (e.g., 0.010" clearance) within a catheter sheath introducer (CSI) which has been introduced through an external incision 174 in the skin of the patient. The knot 144 is pushed through the CSI 170, as shown in FIG. 6. The other end segment 140a is held firmly in the hand of the practitioner. In this manner, the two half hitches are pushed towards and up to an internal incision in the patient. Next, a single half hitch of the same type is formed (e.g., if two right half hitches were initially used, then a single right half hitch is formed) and pushed towards and up to the internal incision with the member 100, but with the practitioner now holding both end segments 140a, 140b securely in one hand. All consecutive loops are advanced in an analogous fashion towards the internal incision and are likewise of the same type, except for the last loop. The last loop is a half hitch of the other type, e.g., if the previous loops were all right half hitches, then a left half hitch is used, thereby creating a square knot, i.e., a tightened knot.

Figure 7A:
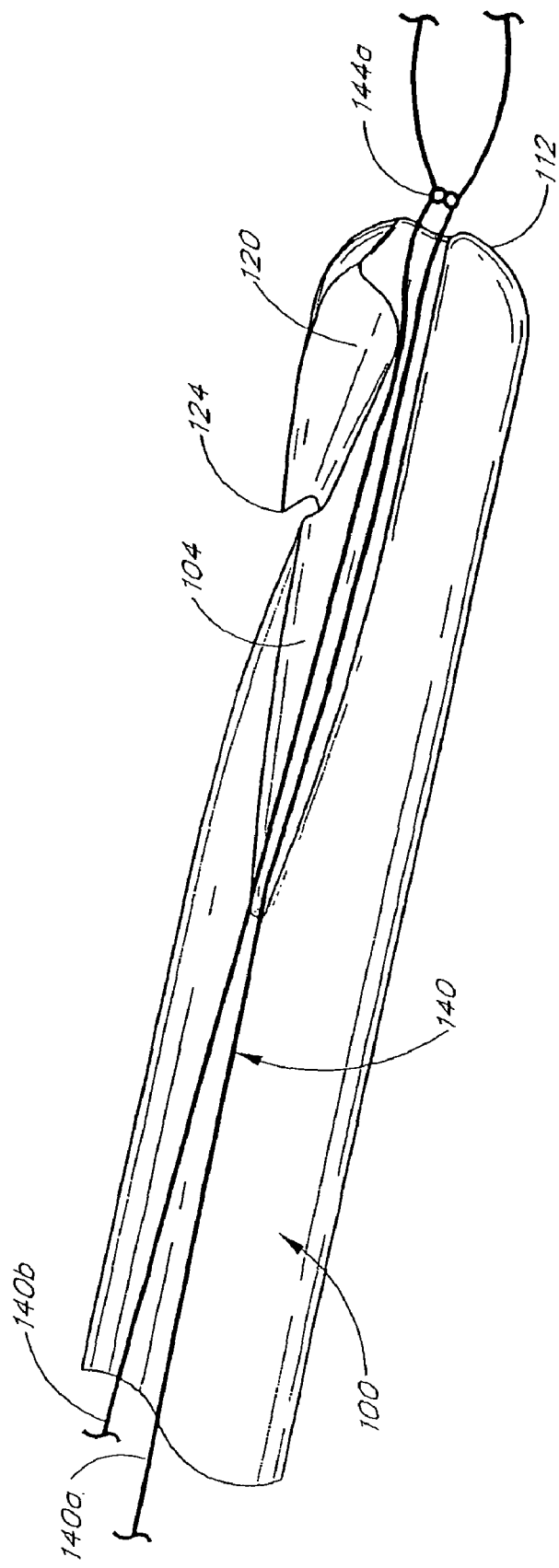
FIG. 7A shows the suture ends drawn across the suture cutter in preparation for cutting the suture ends.
Figure 7B:
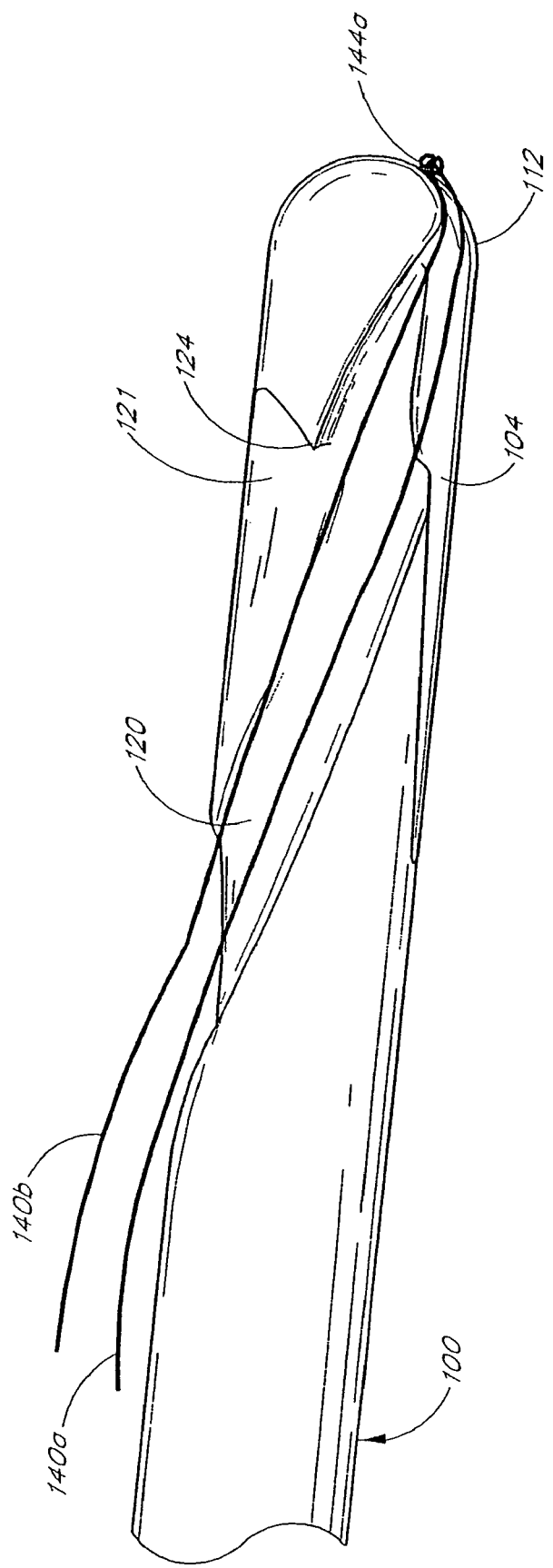
FIG. 7B illustrates the suture ends being cut as the suture cutter is rotated about its longitudinal axis, thereby forcing the suture ends against a cutting element.
Figure 7C:
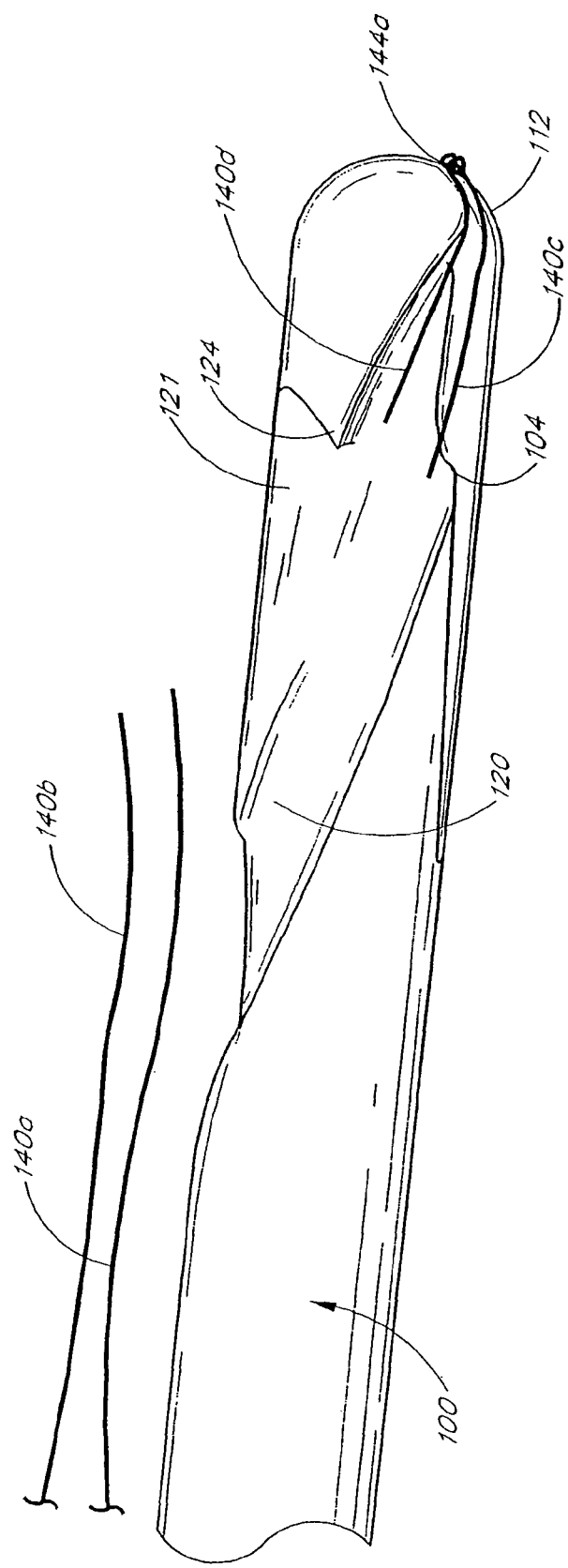
FIG. 7C shows the suture cutter and the suture ends after the suture ends have been cut.

As mentioned, other types of knots and knot tying approaches may be used to form a tightened knot. Once a tightened knot has been formed against the internal incision, the practitioner cuts both end segments 140a, 140b so that no strands are left dangling outside of the patient's external incision 174. This is accomplished most easily by first removing the elongated member 100 completely from the patient while leaving the CSI 170 in place. The practitioner then pulls both end segments 140a, 140b taut and places both segments within the first longitudinal recessed portion 104. The elongate member 100 is reintroduced into the patient through the CSI 170 and pushed towards the tightened knot (at the internal incision) until the distal end portion 112 of the elongate member 100 butts up against the tightened knot. FIG. 7A shows the relationship between the elongated member 100, the suture 140, and the tightened knot 144a at this point. Next, the practitioner rotates the elongated member 100 so that the suture 140 falls into the angled recess 120, where the suture is contacted by the cutting element 124, as shown in FIG. 7B. While holding the suture end segments 140a, 140b taught, the practitioner continues to rotate the tubular member 100, while pulling the member 100 proximally, the force of the cutting element 124 against the suture cuts both end segments 140a, 140b, so that only short, stubby segments 140c, 140d of the suture remain joined to the tightened knot 144a, as shown in FIG. 7C. At this point the loose end segments 140a, 140b are removed from the patient, along with the CSI 170. The external incision 174 is then sutured closed.

Figure 8:
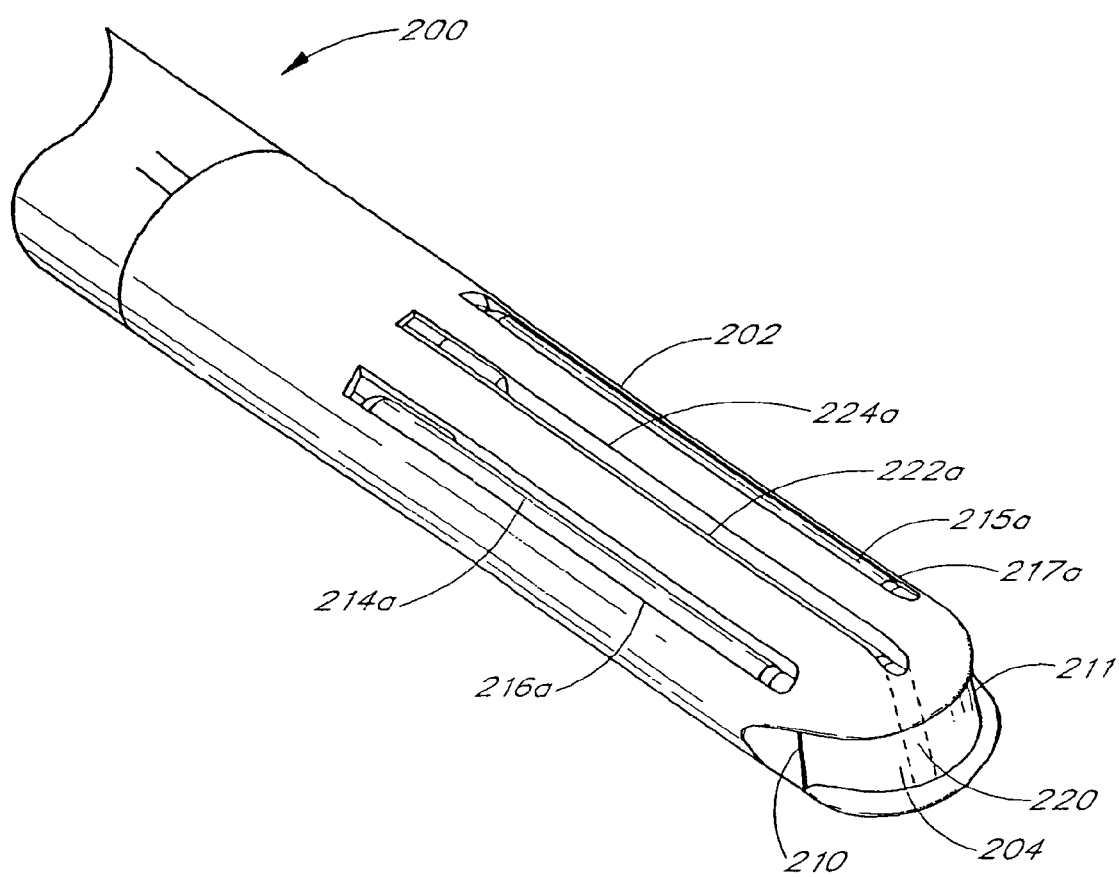
Figure 9:
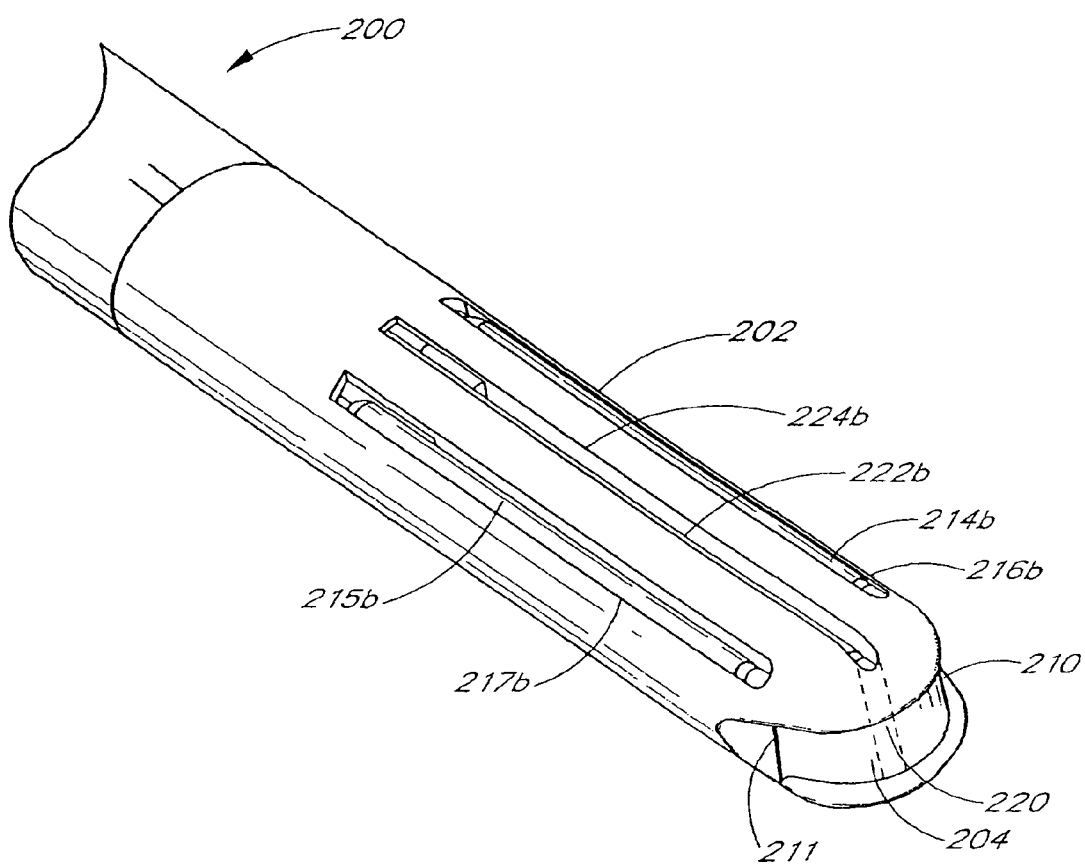

A second suture cutter embodiment 200 is shown in FIG. 8. A recessed, transverse, channel-shaped portion 204 at a distal end 202 of the suture cutter 200 extends from one side of the cutter 200 to the other. The portion 204 is configured for guiding suture strands and optionally for pushing knots. Two side resistive heater elements 210, 211 (e.g., copper) are located on either side of the suture cutter 200 within the channel-shaped portion 204 at respective ends thereof and about 1 cm longitudinally from the tip of the distal end of the cutter. The side resistive heater elements 210, 211 are electrically connected to respective electrically insulated lead lines 214a, 215a which pass through the cutter 200 and are visible through respective grooves 216a, 217a. A centrally located resistive heater element 220 (shown in dashed lines), disposed in the center of the portion 204 at the tip of the distal end 202, is likewise connected to an electrically insulated lead line 222a which is visible through a groove 224a. The resistive heater element 220 resides within the cutter 200 near the recessed portion 204 and is not exposed to the outside environment. FIG. 9 shows the cutter 200 rotated by 180 degrees about its longitudinal axis and illustrates that the resistive heater elements 210, 211 are electrically coupled to electrically insulated lead lines 214b, 215b, respectively, which, together with lead lines 214a, 215a, complete the circuit through the resistive heater elements 210, 211. Likewise, the centrally located resistive heater element 220 is electrically coupled to an electrically insulated lead line 222b which, with the lead line 222a, form an electrical circuit. The lead lines 214b, 215b, 222b are located in respective grooves 216b, 217b, 224b. Side views of the second suture cutter embodiment 200 are illustrated in FIGS. 10 and 11.

Figure 12:
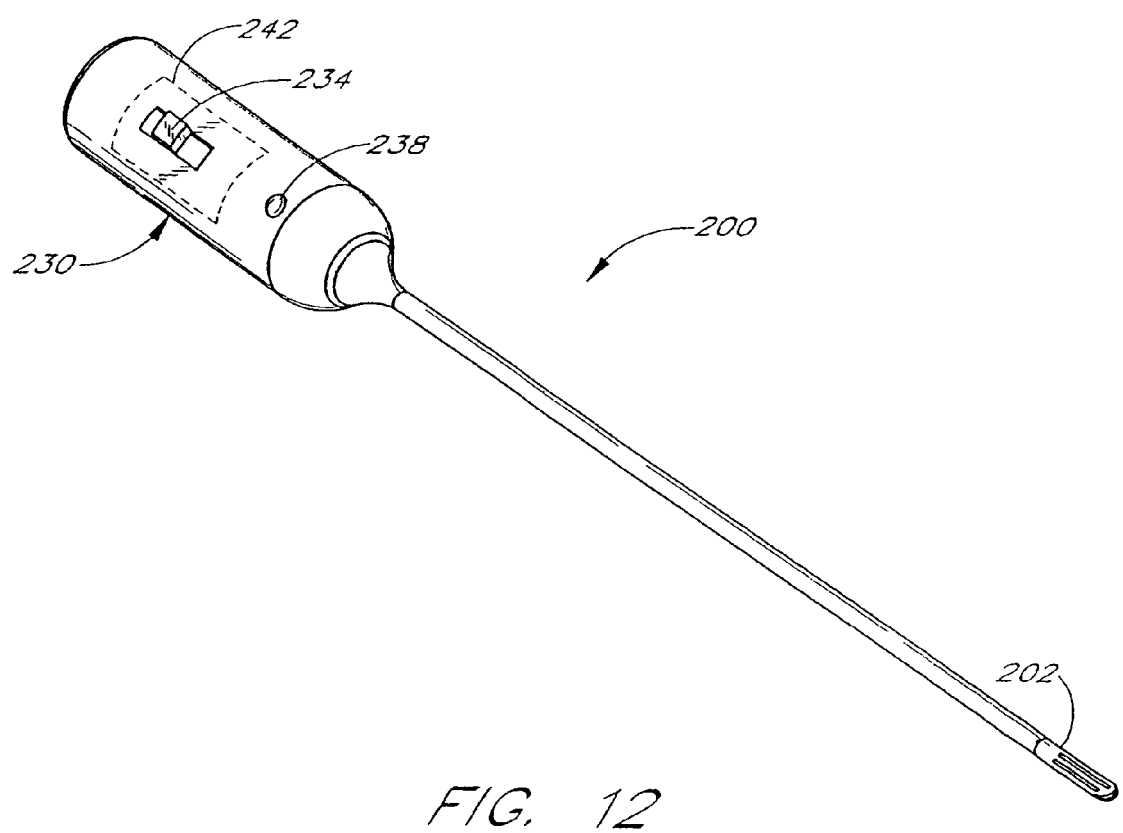

A full length view of the suture cutter 200 is shown in FIG. 12. The suture cutter 200 includes a handle 230 at its proximal end. The handle 230 includes a three-position switch 234 coupled to an LED 238 which indicates whether the switch 234 is off, in the first on-position (for heating the centrally located resistive heater element 220), or in the second on-position (for heating the side resistive heater elements 210, 211). The handle 230 further includes a charging battery 242 (shown in dashed lines). The battery 242 supplies power to the resistive heater elements 210, 211, 220 as controlled by the switch 234.

Figure 13:
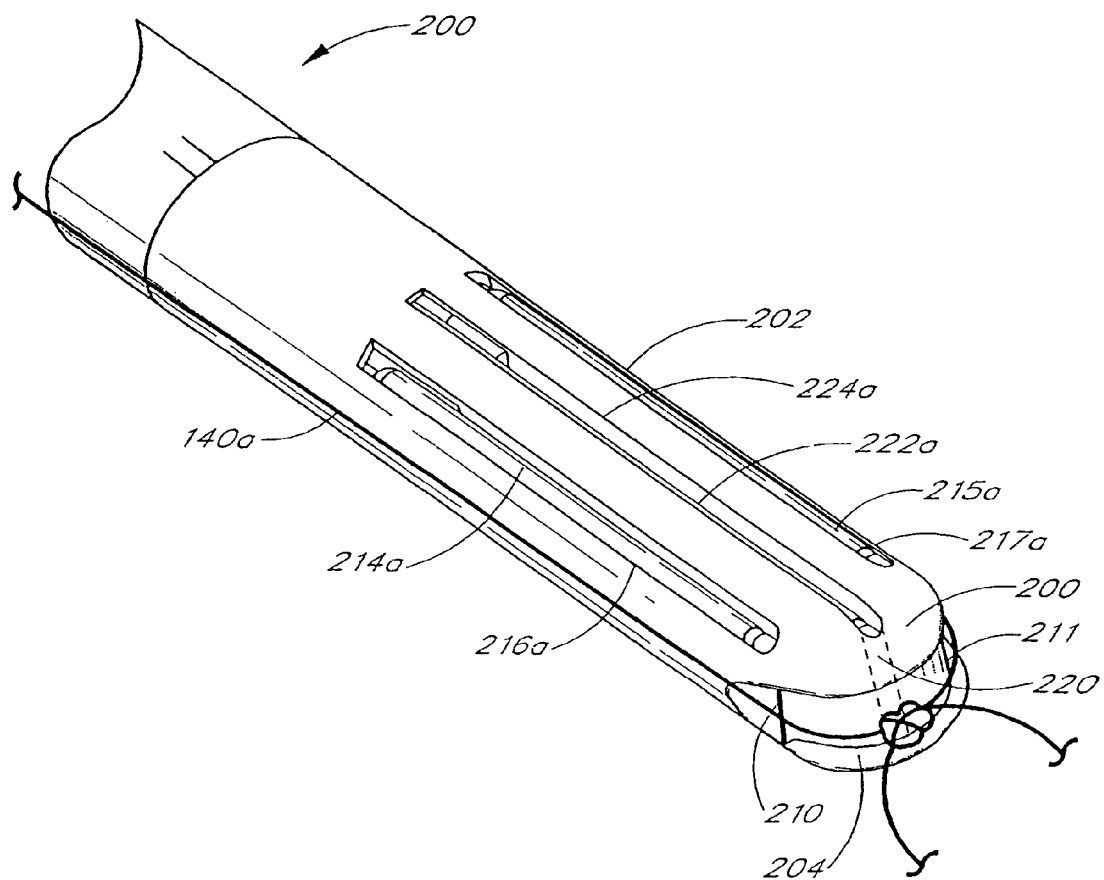
Figure 14:
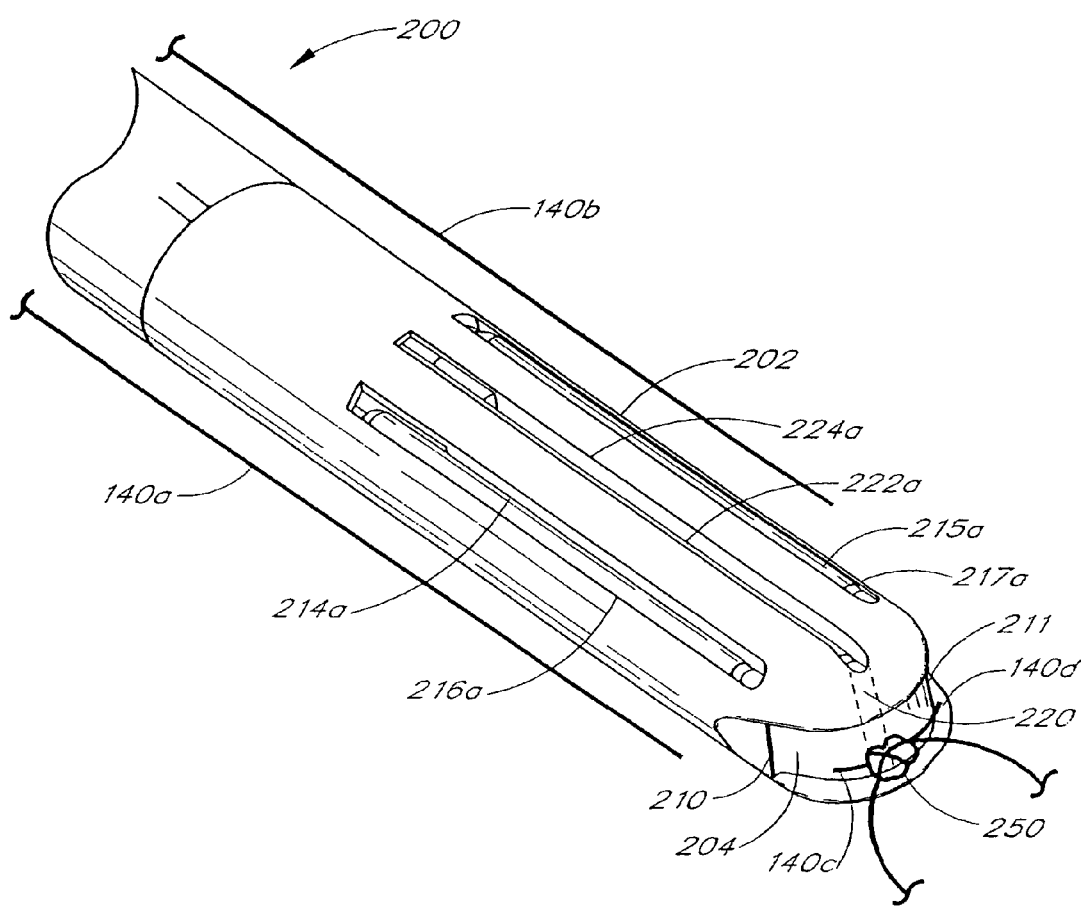

The suture cutter 200 may be used to push a knot in a fashion analogous to that of the first suture cutter embodiment described above. In particular, the recessed portion 204 may advantageously engage a knot which is then pushed by the practitioner through a CSI and towards an internal incision in a patient. Although a tightened knot may be formed, for example, by repeatedly pushing half hitches through the CSI as described above, the suture cutter 200 offers alternatives to this approach. For example, once a knot (or even crossed suture end segments) has been positioned just proximal to the internal incision, power may be supplied to the centrally located resistive heater element 220. As illustrated in FIG. 13, this causes the element 220 to heat up. Sufficient heat is applied to plastically deform the suture material in the knot, by partially melting the suture material to join the end segments together. However, the heat is not so great as to sever the suture material. Next, the two end segments 140a, 140b of the suture 140 are held taut by the practitioner within the channel portion 204 so that they contact the resistive heater elements 210, 211, respectively. Power is then supplied to the elements 210, 211 located on either side of the suture cutter 200. Referring to FIG. 14, the resistive heater elements 210, 211 supply sufficient heat to cause the suture to be severed by melting, leaving short segments 140c, 140d of suture material adjoining the formed knot 250. The end segments 140a, 140b and the suture cutter 200 can then be removed from the patient along with the CSI.

Figure 15:
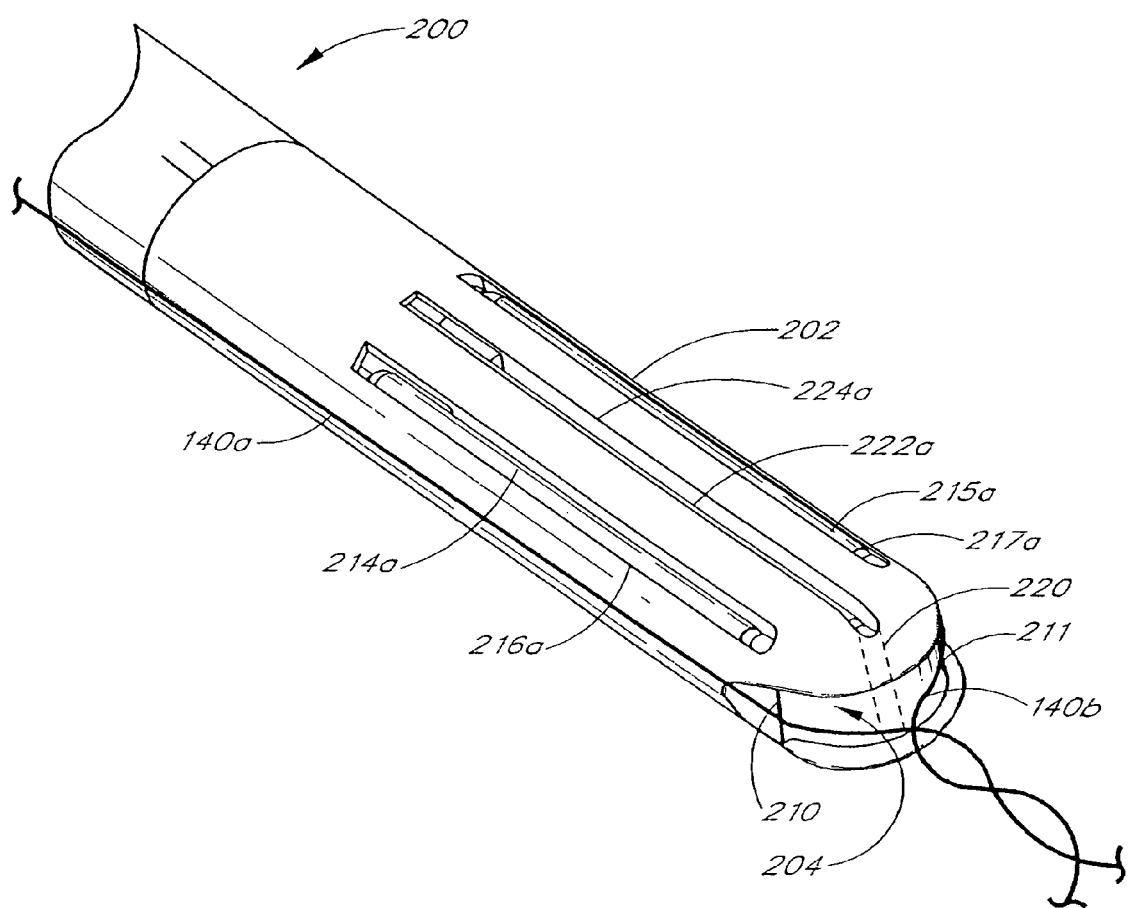

In an alternative method, the two end segments 140a, 140b may be held taut on respective sides of the suture cutter 200 by the practitioner, and the suture cutter 200 is pushed towards the internal incision. When the distal end 202 of the suture cutter 200 is near the internal incision, the suture cutter 200 is rotated about its longitudinal axis, so that the end segments 140a, 140b contact and twist about each other, as shown in FIG. 15. The practitioner may then apply power to the centrally located resistive heater element 220 to fuse the twisted suture and thereby prevent it from unraveling. The twisted suture effectively becomes a knot that is held together by fused suture material. The end segments 140a, 140b may be severed by melting using the side resistive heater elements 210, 211 as described previously. The end segments 140a, 140b and the suture cutter 200 can then be removed from the patient along with the CSI.

A third suture cutter embodiment is shown in FIGS. 16-24. FIG. 16 shows a side view of a first cylindrical member 300 which at one end 302 includes a channel-shaped, recessed, transverse portion 304 for engaging and pushing a knot. An end view of the recessed portion 304 is shown in FIG. 17. At the other end 306 of the cylindrical member 300 is a dome shaped element 308 and four elongate blade members 310 which are circumferentially arranged around the cone-shaped element 308. The end 306 of the cylindrical member 300 is seen more clearly in the end view of FIG. 18. Each of the blade members 310 projects longitudinally and terminates in a terminal end 314 which is rounded or otherwise sufficiently dull that it can not damage tissue. The blade members 310 have longitudinal edges 318, disposed on the outward side thereof, which are sharp so that they can cut through suture material.

Figure 19:
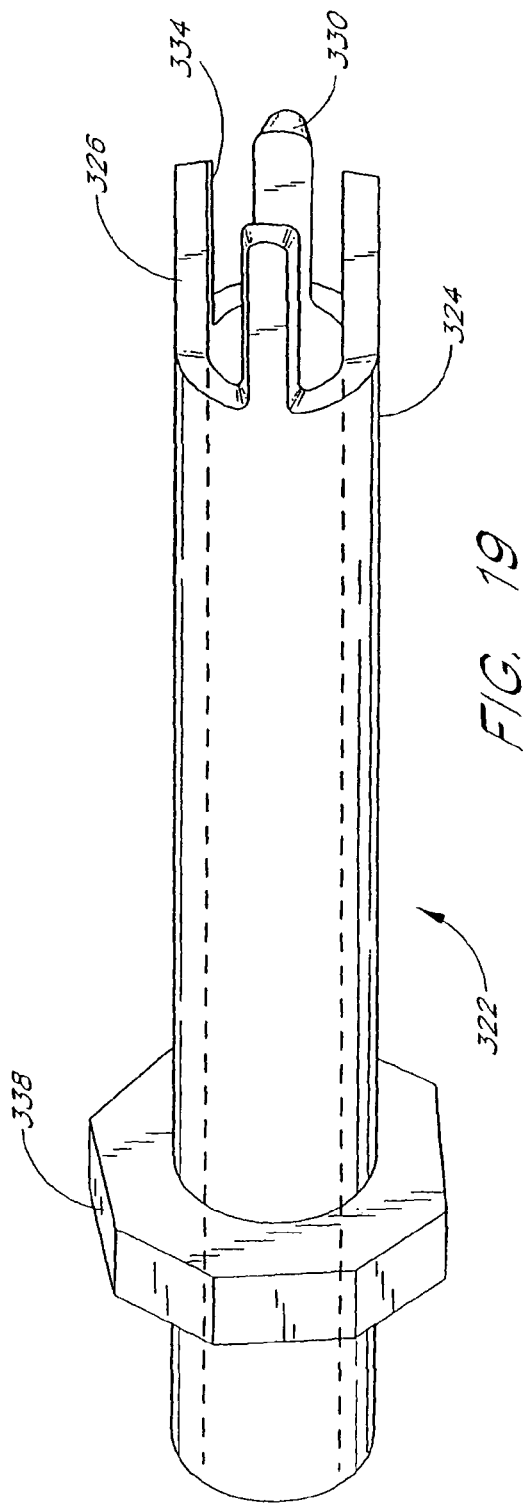
Figure 20:
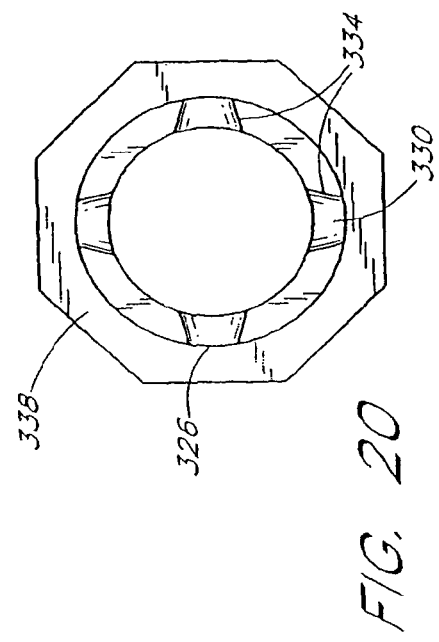

A second cylindrical tubular member 322, illustrated in FIG. 19, has an interior passage sized so that it can be slid over the first cylindrical member 300. At one end 324 of the second cylindrical member 322, four longitudinally extending, elongate blade members 326 are provided which likewise terminate in flattened or rounded ends 330 that are dull. The blade members 326 have longitudinal edges 334 on the inward side thereof which are sharpened for cutting suture material. An end view of the second cylindrical member 322 is shown in FIG. 20. The cylindrical member 322 further includes a extension member 338 such as a hexagonal nut for rotating the second cylindrical member 322.

Figure 21:
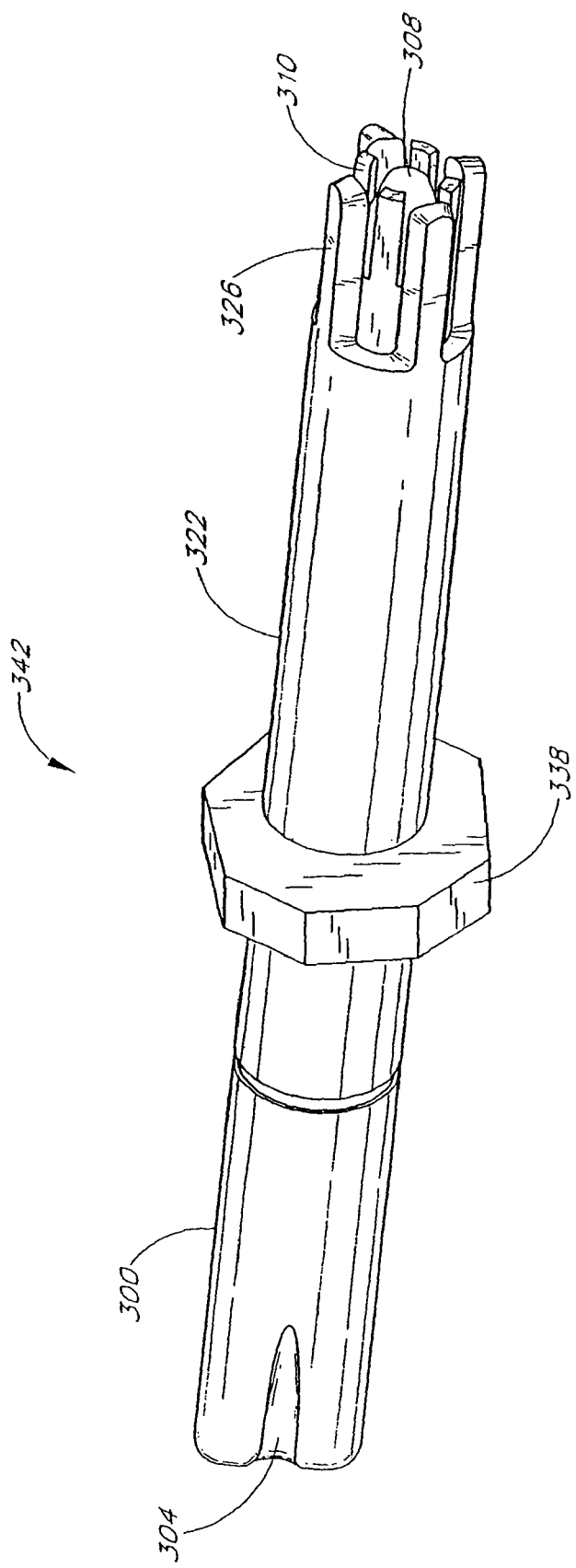
Figure 22:
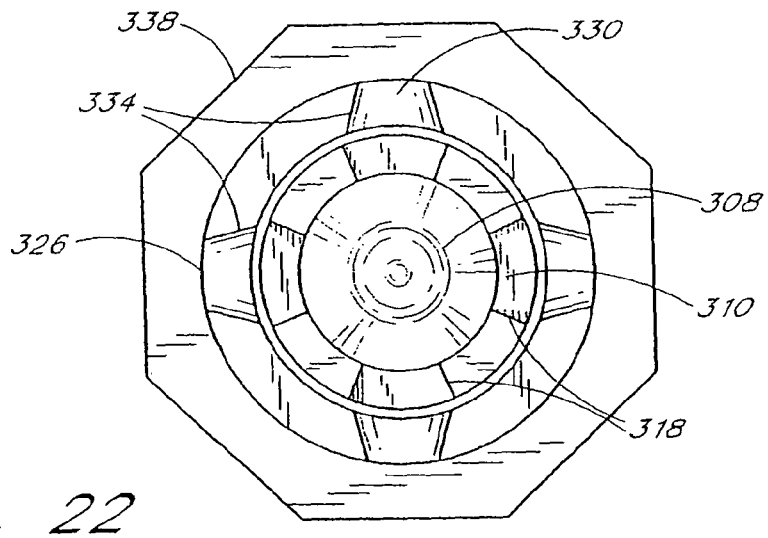

The first and second cylindrical members 300, 322 are operably coupled to form a suture cutter 342 by sliding the second cylindrical member 322 over the first cylindrical member 300, as shown in FIG. 21. The cylinders 300, 322 are rotatable relative to each other, and the blade members 310, 326 are configured so that the sharpened edge 334 of the blade members 326 and the sharp edges 318 of the blade members 310 pass immediately adjacent to each other during rotation. The tolerance between the blade members 310 and the blade members 326 is such that a suture extending between the blade members 310, 326 will be cut when the sharp edges 318 and 334 move past each other. An end view of the device 342 showing the blade members 310, 326 is shown in FIG. 22. The spaces between each pair of blade members 310 form respective slots for receiving a segment of suture.

Figure 23:
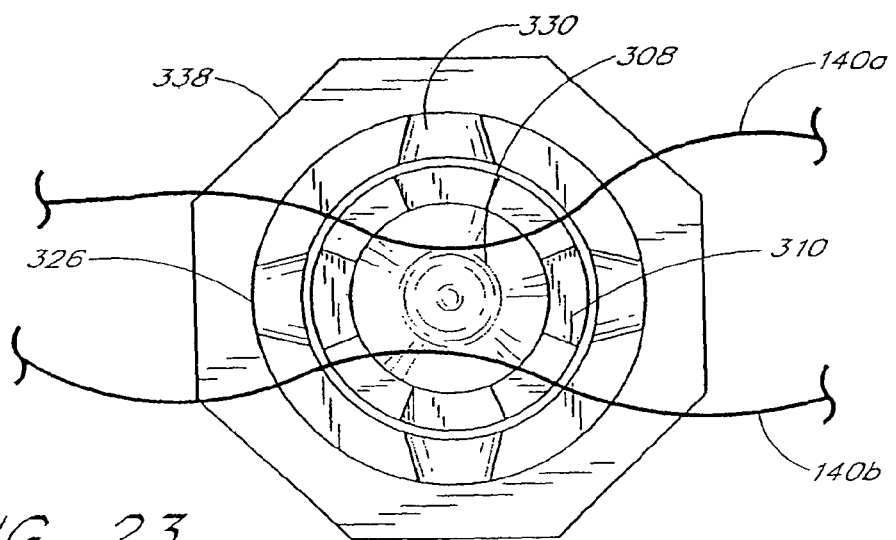
Figure 24:
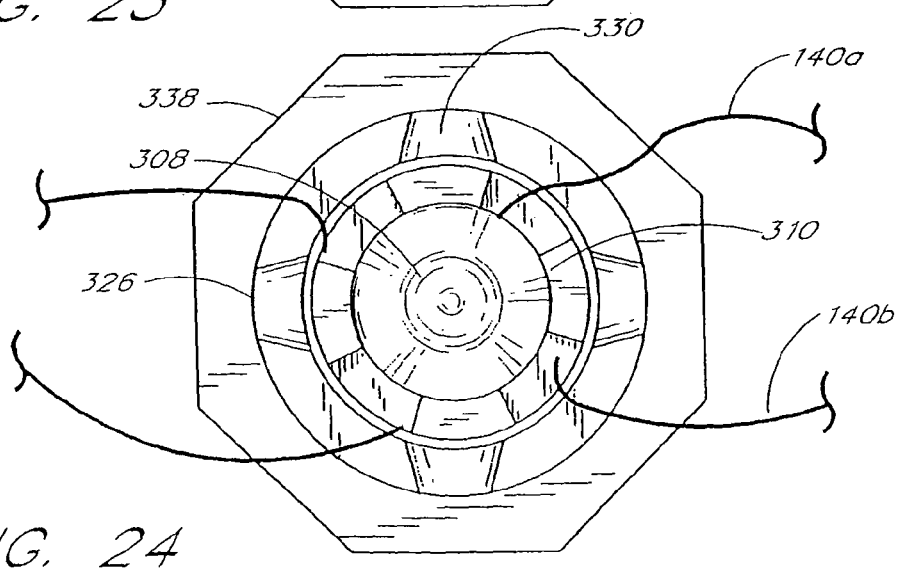

In operation, the practitioner may use the end 302 of the first cylindrical member 300 to push a knot through a CSI towards an incision within a patient and form a tightened knot just proximal to the internal incision, as discussed in connection with the other methods disclosed herein. The device 342 is then retracted from the patient and turned around so that the end of the device with the blade members 310, 326 faces the CSI. Each of the end segments 140a, 140b of a suture is placed into different suture receiving slots formed by the blade members 310, as illustrated in FIG. 23. The device 342 is reinserted into the patient and pushed through the CSI towards the knot (which is proximal to the internal incision) until the dome shaped element 308 contacts the knot. At this point, the practitioner rotates the second (outer) cylindrical member 322 with respect to the first (inner) cylindrical member 300 by grasping and turning the extension member 338. As a result of this rotation, the suture material is cut between the blade members 310, 326, as shown in FIG. 24.

Figure 25:
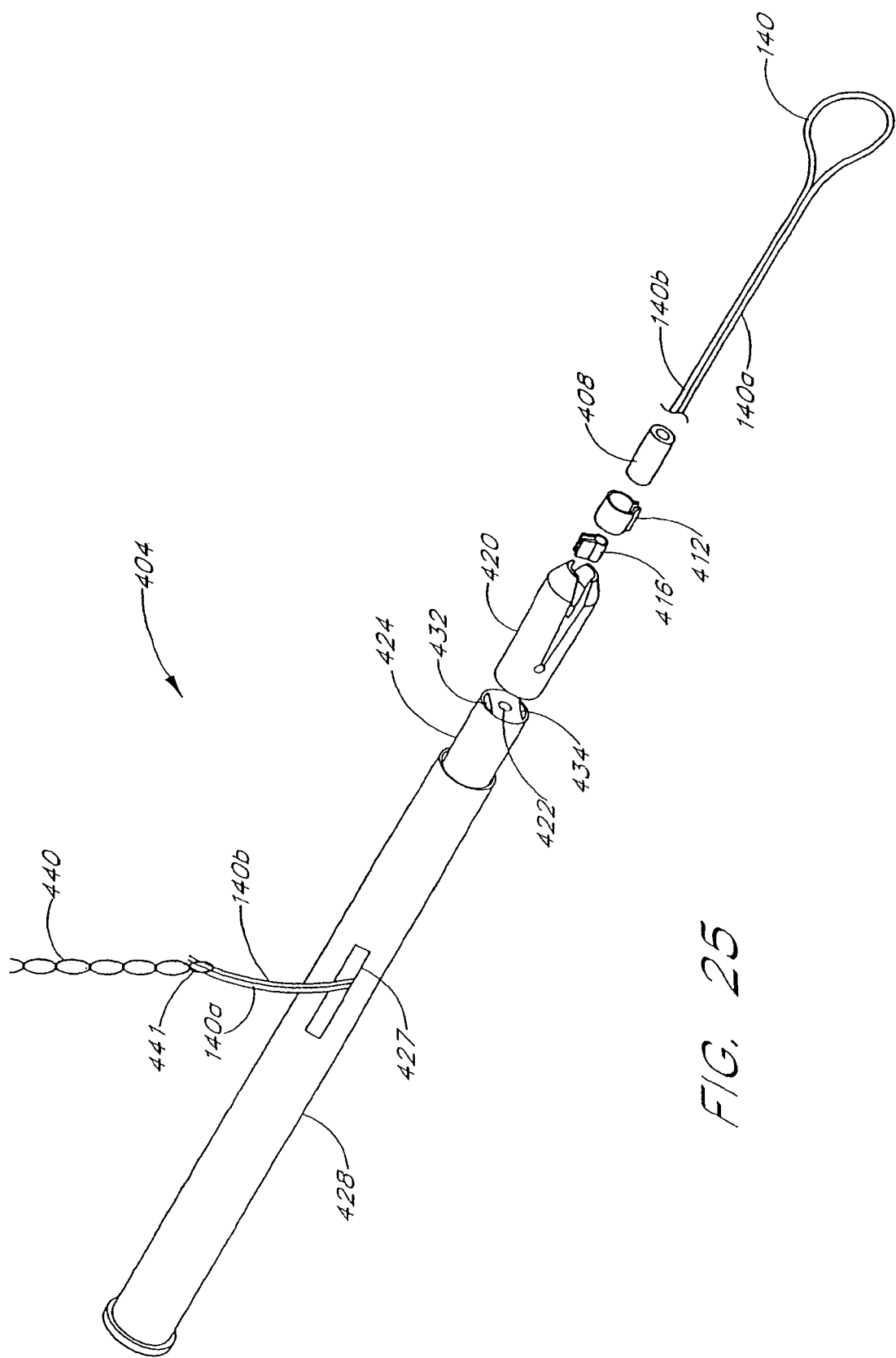
Figure 26:
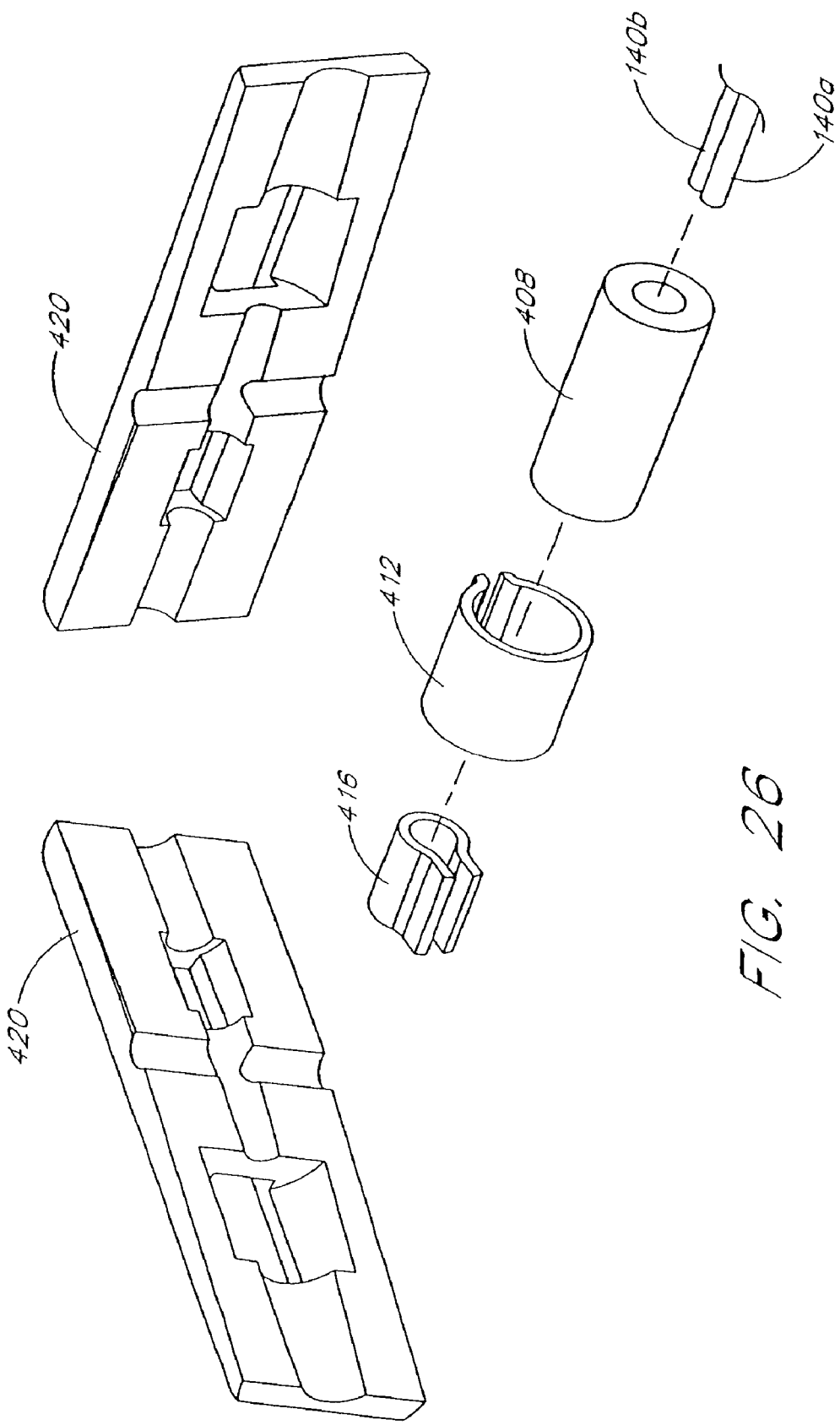

A fourth embodiment is shown and described with respect to FIGS. 25-28. The device functions both as a knot former and suture cutter. An exploded, isometric view of the distal end 404 of the device is shown in FIG. 25. The two end segments 140a, 140b of a loop of the suture 140 pass through a suture collar or cylinder 408 which is preferably made of the same material as the suture itself, e.g., monofilament polypropylene. The two end segments 140a, 140b also pass through a welding element 412, a cutting element 416, a compression tip 420, a lumen 422 in a multi-lumen inner tube 424, a side hole 426 (FIG. 28) in the inner tube, and a side slot 427 in an outer compression tube 428 which registers with the hole 426. As illustrated most clearly in the cutaway of FIG. 26, the welding element 412 and the cutting element 416 are configured such that they make a good mechanical contact with the inside of the compression tip 420. Prior to actuation, the suture collar 408 is placed within the welding element 412 so that the proximal end of the suture collar is flush with the proximal end of the welding element, whereas the distal end of the suture collar 408 extends slightly beyond the distal end of the welding element.

Figure 27:
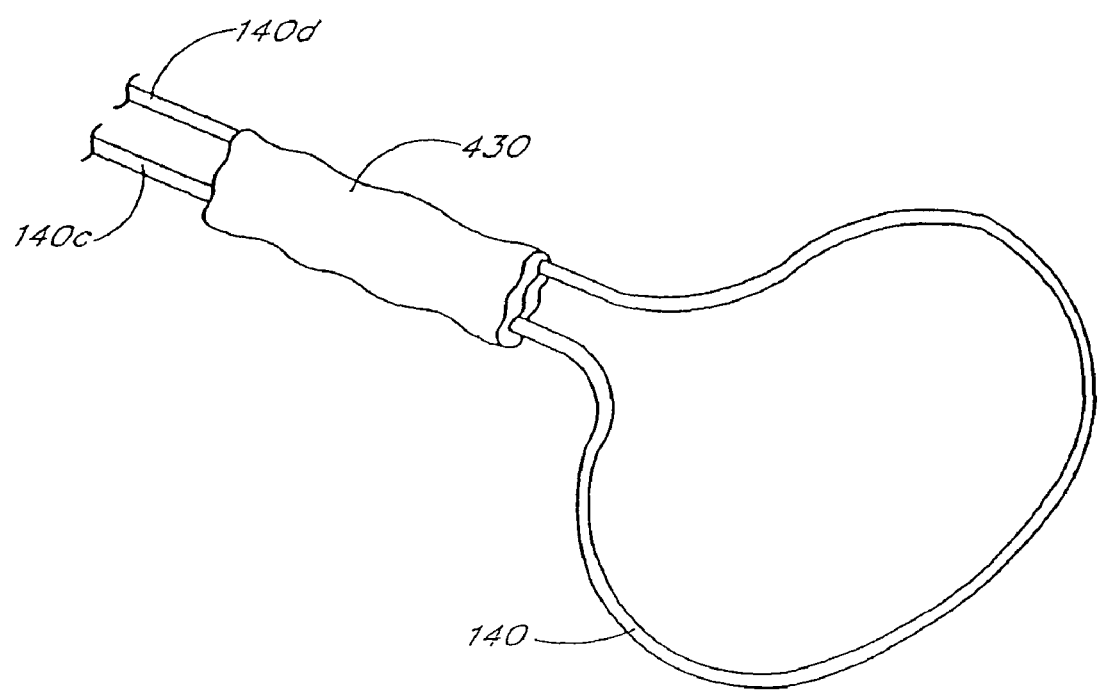

The compression tip 420 is integrally joined to the inner multi-lumen tube 424, which may be the same material as the compression tip (e.g., plastic), or alternatively, the compression tip may be metal with the inner tube 424 being plastic. The outer compression tube 428 is slidably mounted on the inner tube 424 and the compression tip 420. The compression tip 420 has a pair of relief slots which allow its distal end portion to flex inwardly. When the outer compression tube 428 is slidably forced over the compression tip 420, the compression tip flexes and presses the suture collar against the end segments 140a, 140b. The suture collar 408 and the end segments 140a, 140b may then be fused together by activating the welding element 412 to apply heat to the suture collar 408. Sufficient heat is applied by the welding element 412 to plastically deform the collar and partially melt the suture material to cause the suture ends and suture collar to fuse together. The heat, however should not be so great as to sever the suture. Such fusion forms a bulb or fused mass 430 in the suture 140 which effectively acts as a knot, as shown in FIG. 27. The end segments 140a, 140b proximal to the suture collar 408 may then be severed from the suture collar by activating the cutting element 416 to apply sufficient heat to the suture ends so that they are severed. The cutting element 416 is spaced proximally from the suture collar so that such cutting leaves behind short, stubby segments 140c, 140d of suture material attached to the mass 430 (see FIG. 27). The welding element 412 and the cutting element 416 comprise resistive elements that generate heat when electrical current is supplied. In the case of the welding element 412, heat is transferred to the suture collar 408 and the end segments 140a, 140b, so that the suture cylinder and the suture strands meld or fuse together. On the other hand, the heat applied by the cutting element 416 to the end segments 140a, 140b is sufficient to melt through the strands. After the welding element 412 and the cutting element 416 have been activated in turn and the mass 430 is formed, the suture cutter 400 may be cleaned and reused or simply discarded in favor of a new suture cutter.

Figure 28:
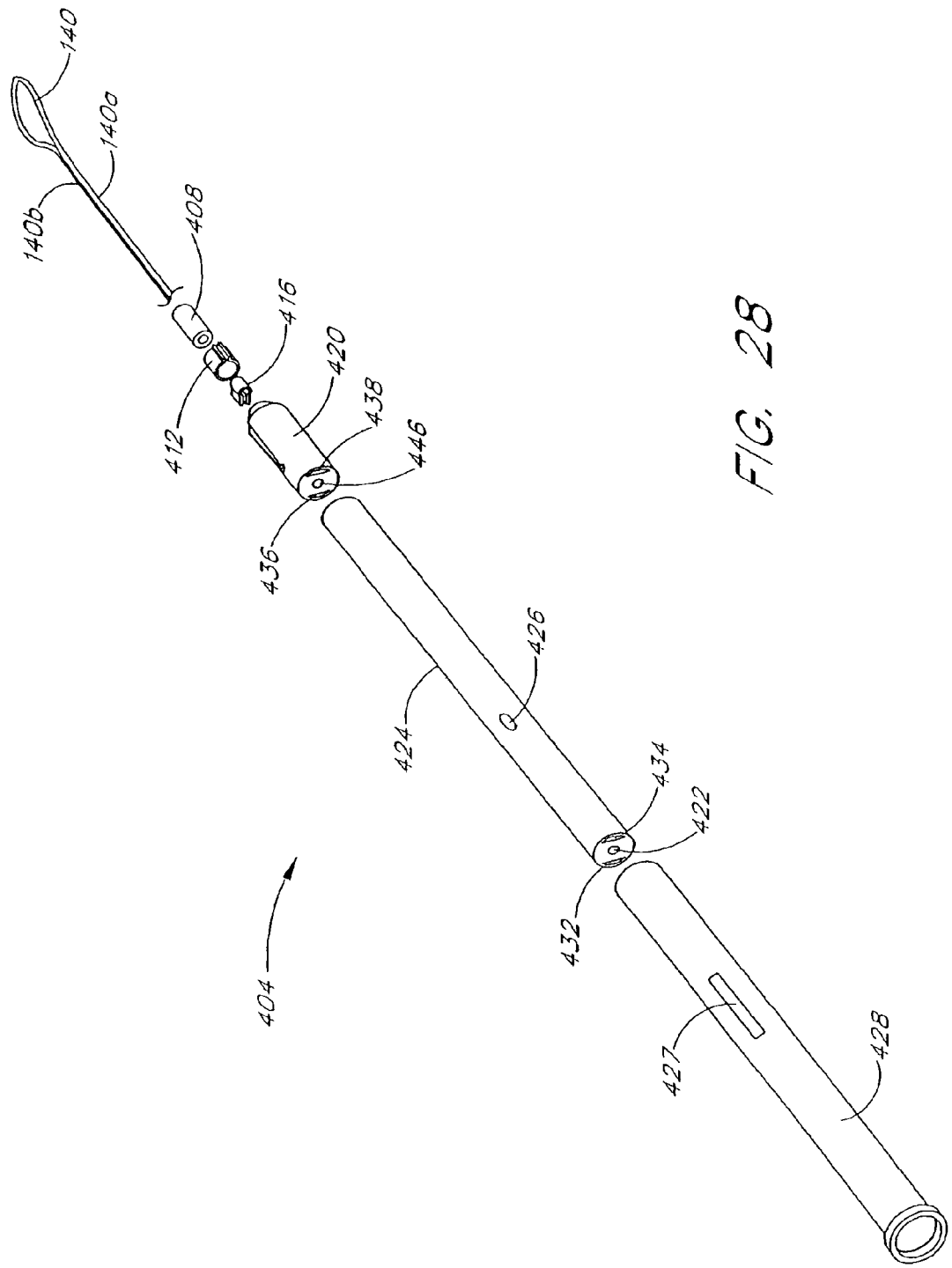

Electrical current is supplied to the welding element 412 and to the cutting element 416 through respective pairs of lead lines (not shown), which pass through lumens 432, 434 in the inner extrusion tube 424 and lumens 436, 438 in the compression tip 420. The lumens 436, 438 are shown in FIG. 28. When the inner extrusion tube 424 and the. compression tip 420 are joined during the fabrication process, the lumens 432, 434 are aligned with the lumens 436,438, respectively, so that the lumens 432, 436 form one continuous lumen, as do the lumens 434, 438. The lumen pair 432, 436 may be used to carry lead lines to the welding element 412, whereas the lumen pair 434, 438 may be used to carry lead lines to the cutting element 416. (The lumen 422 in the inner extrusion tube 424 and a lumen 446 in the compression tip 420 are used to receive the end segments 140a, 140b.) A power supply (not shown) connected to the lead lines may be advantageously programmed so that the welding element 412 and the cutting element 416 are supplied with the appropriate amount and duration of current.

The end segments 140a, 140b may be loaded into the suture cutter 400 by drawing them through the suture collar 408 (which is surrounded by the welding element 412), the cutting element 416, the compression tip 420, the lumen 422 in the inner extrusion 424, the hole 426 in the inner extrusion 424, and the slot 427 in the outer compression tube 428. For this purpose, a suture leader comprising a wire 440 having a grasping portion 441 (see FIG. 25) at its distal end for holding the end segments 140a, 140b may be used, such as that described in Applicant's copending Application Ser. No. 09/571,759 entitled "Knot Pusher", filed on May 15, 2000. The wire 440 is passed through the slot 427 and is pushed distally until the grasping portion exits the suture collar 408. The end segments 140a, 140b are then inserted into a loop of wire at the grasping portion to secure the segments to the wire 440. The wire is then retracted back through the distal end 404 of the suture cutter 400. The slot 427 may be 1-2 cm in length and is aligned with the hole 426, so that when the outer compression tube 428 is urged forward (say, 5 mm) to compress the compression tip 420, the end segments 140a, 140b are not caught between the inner extrusion 424 and the outer compression tube 428.

It will be understood by those skilled in the art that embodiments similar to the one shown in FIGS. 25-28 may be employed which rely either on (i) compression forces alone (without the use of a thermal element) to secure the suture collar 408 to the suture end segments 140a, 140b, or alternatively, (ii) a thermal element alone (without the use of a compression tip) to fuse the suture collar 408 to the suture end segments 140a, 140b.

Figure 29:
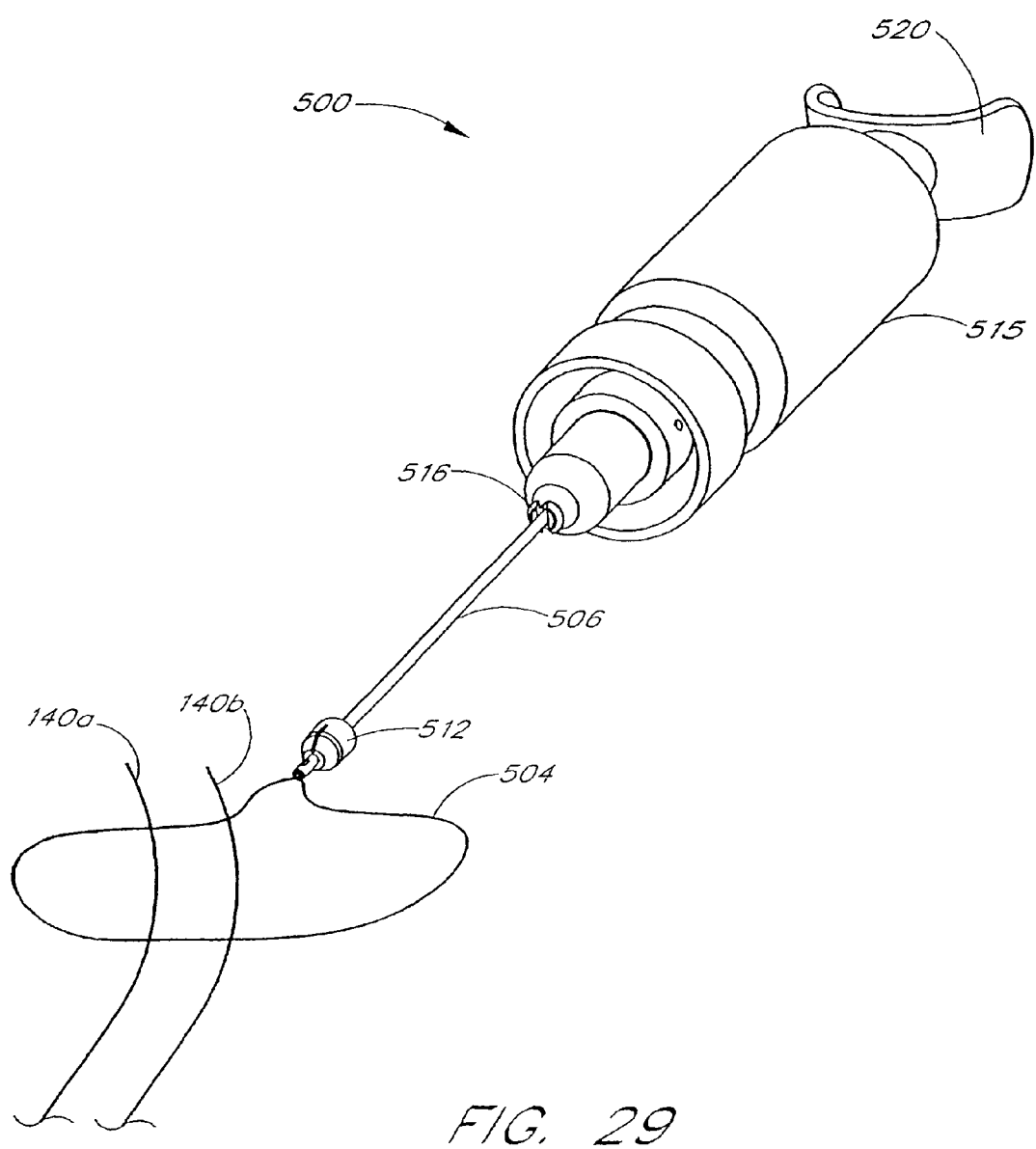
Figure 30:
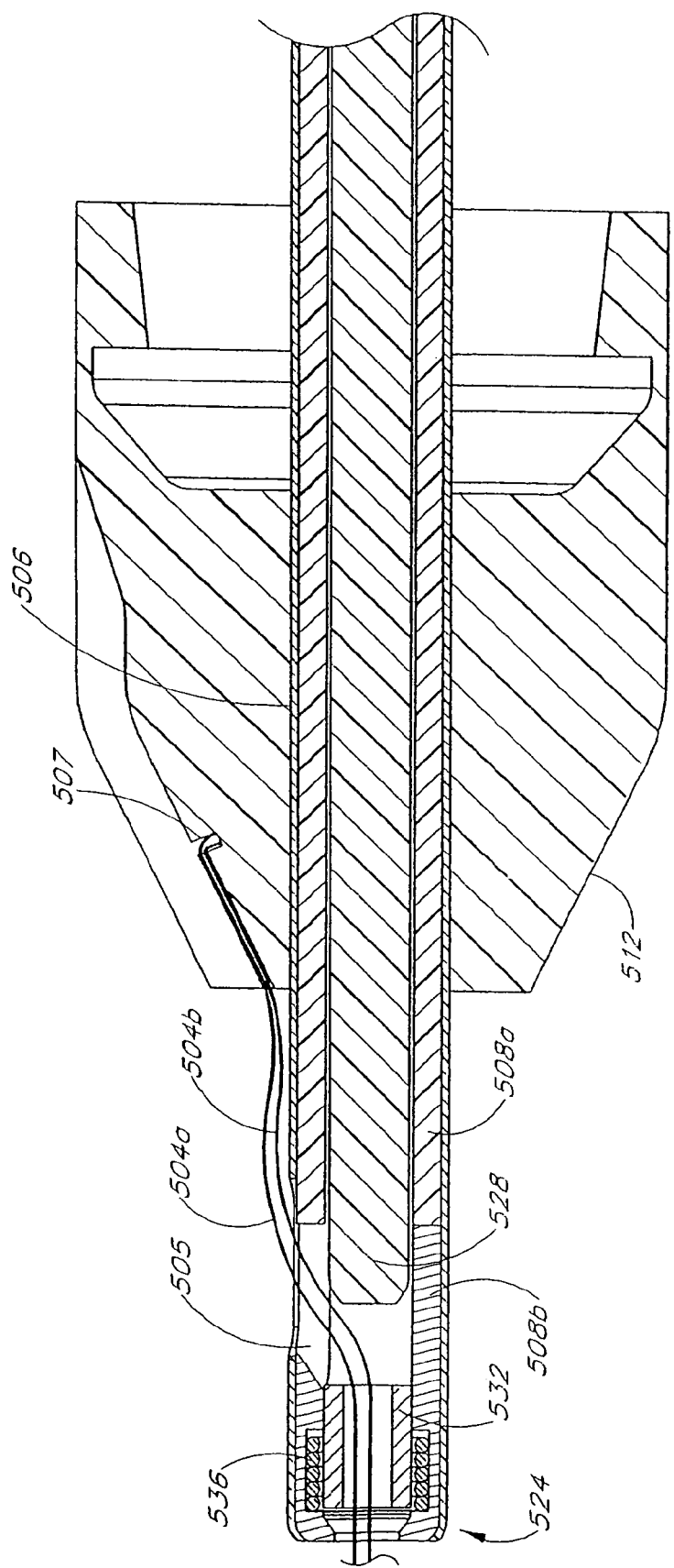

FIGS. 29-33D illustrate a fifth embodiment 500 which acts as a suture cutter while effectively forming a knot as well. As illustrated, the cutter 500 comprises a hypotube 506 that extends from a main body 515. A carriage member 512 is slidably mounted to ride over the hypotube 506. As shown in FIGS. 29 and 30, a lasso 504 comprised of a loop of flexible line, such as a strand or string, has end portions 504a, 504b that are attached to the carriage member 512. When the carriage is at the distal end of the hypotube 506, the loop is open and extends forward of the hypotube so as to receive and surround end segments 140a, 140b of a suture 140. By way of example, the lasso 504 may be comprised of a 0.006" diameter silk strand.

As best shown in FIG. 30, the end portions 504a, 504b of the lasso 504 extend through an opening in the distal end of the hypotube 506 and out of a side window 505 of the hypotube. The terminal ends of the portions 504a, 504b may be secured within a recess 507 of the carriage member 512 with a bonding material such as cyanoacrylate. Secured within the hypotube 506 is a tubular member that includes a proximal tubular portion 508a and a distal tubular portion 508b which have been bonded together. The proximal portion 508a may be plastic, and the distal portion 508*b* is preferably a high temperature plastic. A plunger 528 is mounted to slide longitudinally within the lumen of the tubular members 508*a*, 508*b*. A suture collar 532 comprising a generally cylindrical tubular member is mounted distal to the plunger 528, in spaced relationship thereto, and within a distal portion 524 of the hypotube 506. The plunger 528 is sized to apply force to the proximal end of the suture collar 532. Thus, the lasso 504 extends from the carriage 512 through the window 505, between the plunger 528 and suture collar 532, through the central bore of the suture collar 532, and out of the distal end of the hypotube 506.

Figure 31:
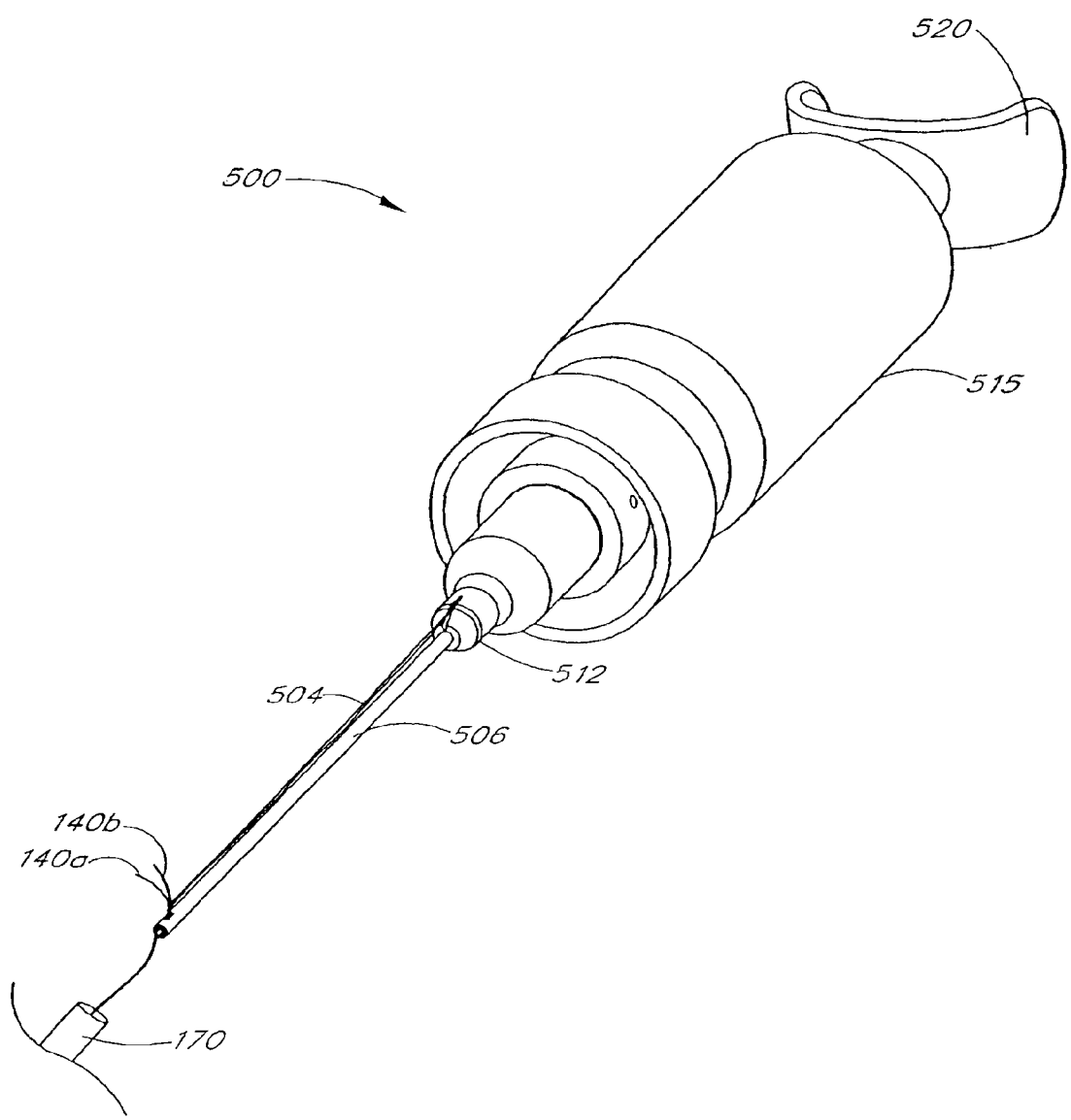
Figure 32:
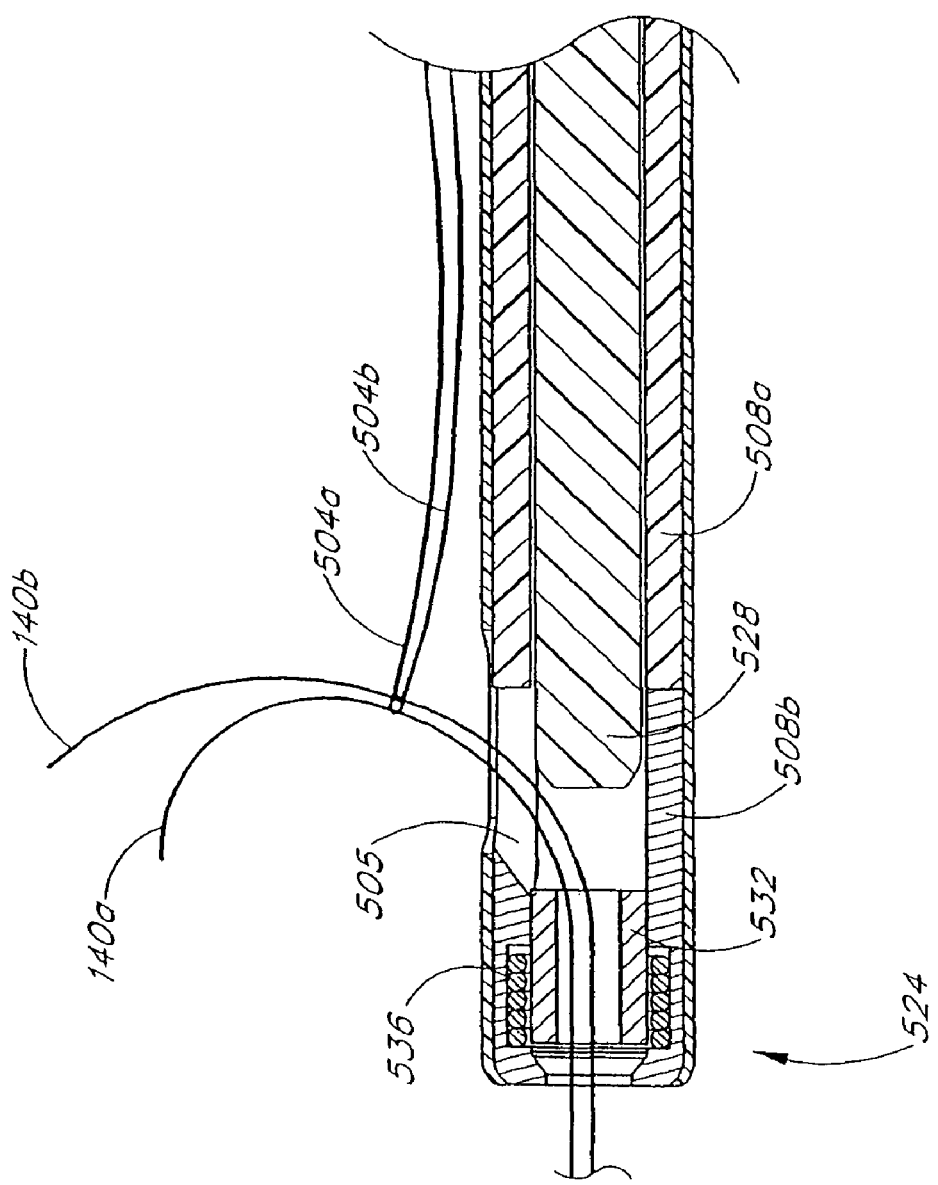

The carriage member 512 slides over the hypotube 506, so that the practitioner may retract (or advance) the carriage member with respect to the hypotube. As mentioned above, when the carriage 512 is advanced to the distal end of the hypotube 506, the lasso 504 is fully open so as to receive suture end segments 140*a*, 140*b*. As the carriage member 512 is retracted, the end portions 504*a*, 504*b* of the lasso 504 are pulled in a proximal direction, so that the size of the loop progressively decreases and the lasso 504 tightens around the suture end segments 140*a*, 140*b*, with the lasso pulling the segments 140*a*, 140*b* into the distal end of the hypotube 506. As the practitioner continues to retract the carriage member 512, the lasso 504 is pulled through the window 505, and the suture end segments 140*a*, 140*b* are carried by the lasso through and out of the window 505 in a proximal direction. As shown in FIG. 31, the carriage member 512 may be completely retracted until it reaches a detent member 516 (seen in FIG. 29) which holds the carriage member in a proximal position. At this point, the entire lasso 504 has been pulled from the window 505 such that the lasso is free to enlarge and is no longer tightly holding the proximal ends of the suture end portions 140*a*, 140*b* which now hang loosely outside the hypotube 506, as illustrated both in FIG. 31 and the cross sectional view of FIG. 32.

Figure 33A:
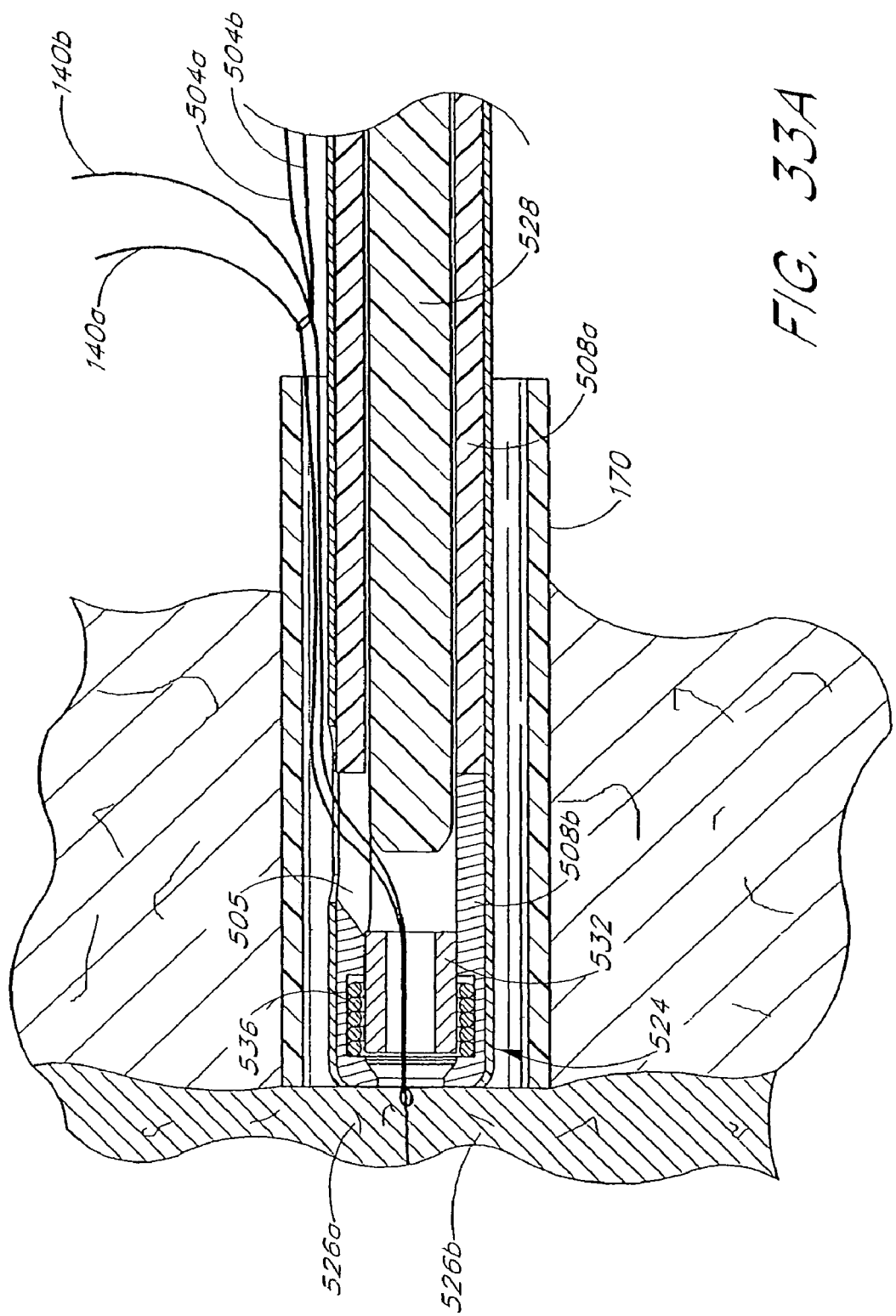

Referring to FIGS. 33A, 33B, 33C, and 33D, the practitioner then holds the ends of the suture and advances the hypotube 506 into the patient and toward the suture site through a catheter sheath introducer (CSI) 170. The distal portion 524 of the hypotube 506 is positioned at the suture site next to tissue portions 526*a*, 526*b* within the patient through which the suture 140 passes, so as to draw the tissue portions 526*a*, 526*b* together. Referring to FIG. 33A, the plunger 528, which may be comprised of a hard, high temperature plastic, is then moved distally by applying force to a handle 520 (FIG. 31). Such distal movement drives the plunger against the suture collar 532 which surrounds the suture end segments 140*a*, 140*b*.

Figure 33B:
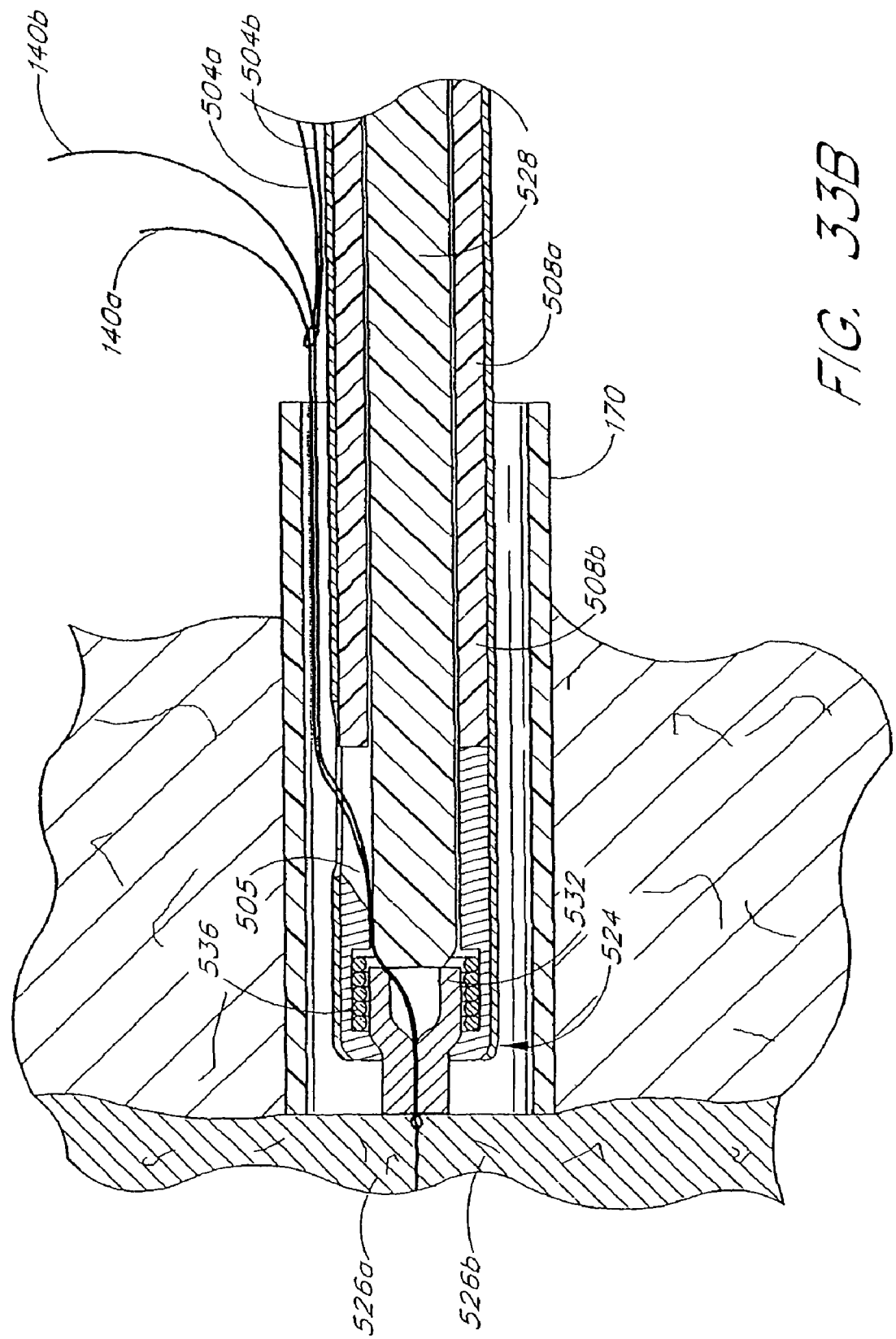
Figure 33C:
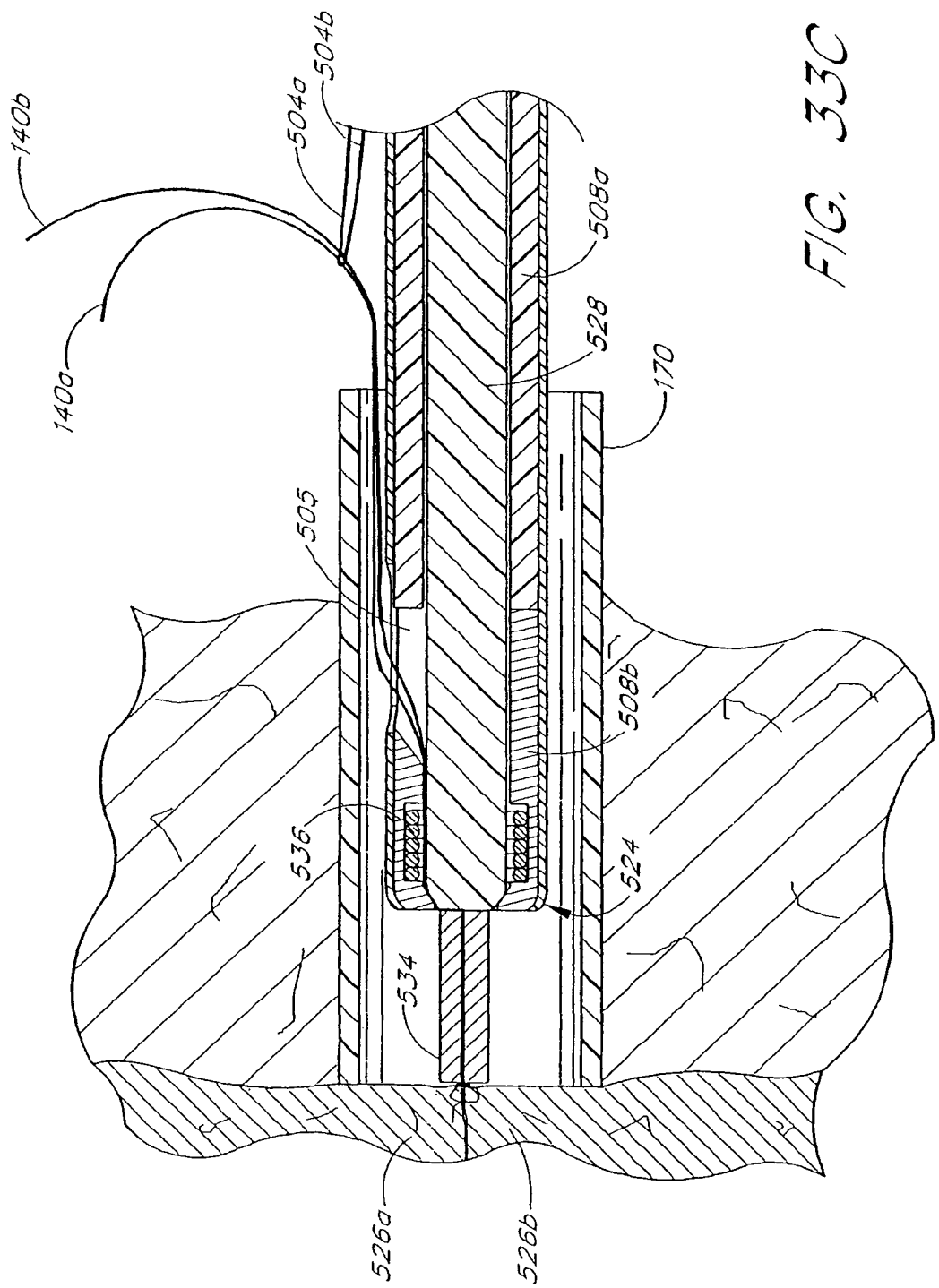

As illustrated in FIG. 33B, a coiled heating element 536 surrounds the suture collar 532. The collar 532 melts or deforms when subjected to heat and may be comprised of the same material as the suture 140, e.g., polypropylene. As the plunger 528 is advanced distally against the suture collar, the heating element is activated to soften the suture collar 532. The distal end of the hypotube has an annular inward projection which forms an opening that is significantly smaller than the diameter of the suture collar 532 so that application of longitudinal force to the collar 532 by the plunger 528 compresses the heated collar against the annular projection. Such compression causes the collar to plastically deform inwardly around and against the suture ends 140*a*, 140*b*, so as to close the opening through the collar 532. In this way, the suture collar 532 is effectively extruded out the distal portion 524 of the hypotube 506. As illustrated in FIG. 33C, such extrusion causes the collar 532 and suture end segments 140*a*, 140*b* to fuse together into a fused mass 534 which effectively acts as a knot (similar to the fused portion 430 of FIG. 27) to keep together the tissue portions 526*a*, 526*b* that have been sutured. To this end, the distal end of the fused mass 534 is preferably adjacent the tissue portions 526*a*, 526*b*.

Figure 33D:
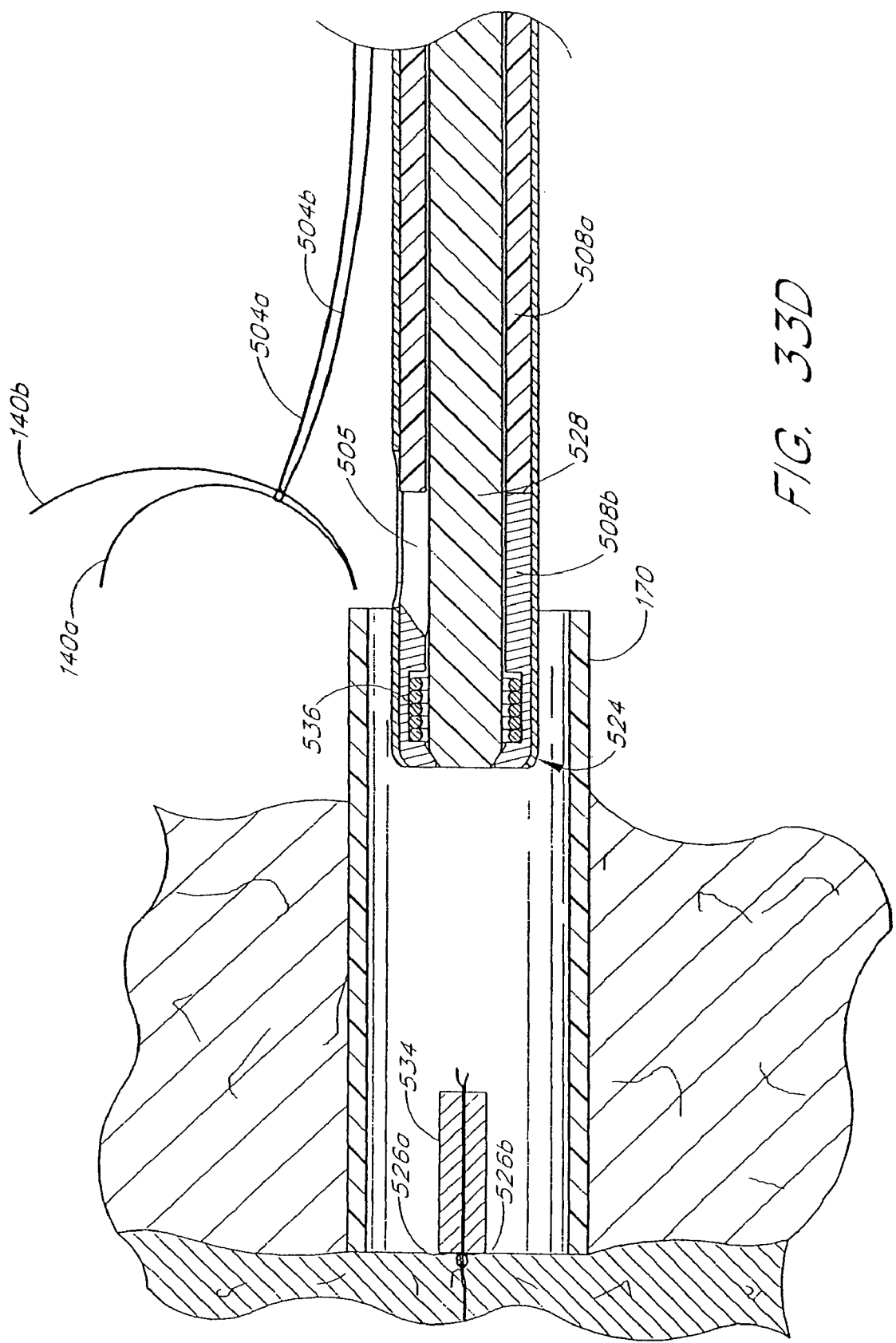

After the fused mass 534 is formed, the portions of the free ends of the suture that extend from the mass will be adjacent to and exposed to the coiled heating element 536 (since the fused mass 534 is now outside the hypotube—see FIG. 33C). The heating element 536 is activated to sever the end segments 140*a*, 140*b* from the rest of the suture 140. The practitioner may then withdraw the device 500 from the CSI 170 and out of the patient, leaving the fused mass 534 behind in the patient, as shown in FIG. 33D. While the preferred embodiment utilizes both heat and compression to cause the collar 532 to lock the suture end portions together, it will be appreciated that other embodiments may use only compression, without heat, and still other embodiments may use only heat, without compression.

Although this invention has been described with reference to specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. An apparatus, comprising:
    a receptacle for juxtaposing portions of a suture to be connected to each other;
    a first heating element positioned to apply heat to the juxtaposed suture portions such that the juxtaposed suture portions are fastened together;
    a second heating element positioned near the first heating element to sever at least one suture end portion, the second heating element being configured for operation independent from the first heating element; and
    a collar positioned at least partially within the receptacle and configured to surround the juxtaposed suture portions, said first heating element disposed to apply heat to said collar;
    wherein said first heating element fuses the collar to the suture portions.

* * * * *